US012761215B2

(12) United States Patent
Ota et al.

(10) Patent No.: US 12,761,215 B2
(45) Date of Patent: Oct. 13, 2026

(54) CELL ANALYSIS DEVICE, CELL DETERMINATION METHOD, AND PROGRAM

(71) Applicant: The University of Tokyo, Tokyo (JP)

(72) Inventors: Sadao Ota, Tokyo (JP); Yuichiro Iwamoto, Toyko (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 921 days.

(21) Appl. No.: 17/937,028

(22) Filed: Sep. 30, 2022

(65) Prior Publication Data

US 2023/0107603 A1 Apr. 6, 2023

Related U.S. Application Data

(63) Continuation of application No. PCT/JP2021/013937, filed on Mar. 31, 2021.

(30) Foreign Application Priority Data

Apr. 1, 2020 (JP) ................................ 2020-065988

(51) Int. Cl.
*G01N 33/537* (2006.01)
*G01N 15/10* (2024.01)
(Continued)

(52) U.S. Cl.
CPC ......... *G01N 33/537* (2013.01); *G01N 15/147* (2013.01); *G01N 15/1492* (2024.01);
(Continued)

(58) Field of Classification Search
CPC ............. G01N 33/537; G01N 15/1492; G01N 15/147; G01N 33/582; G01N 2015/1006; G01N 2015/1481
See application file for complete search history.

(56) References Cited

U.S. PATENT DOCUMENTS

2016/0091428 A1* 3/2016 Yokoyama ......... G01N 15/1012 435/6.1
2017/0166959 A1 6/2017 Hashimoto et al.
2020/0131562 A1 4/2020 Yachie et al.

FOREIGN PATENT DOCUMENTS

WO 2015/166768 A1 11/2015
WO 2018/203576 A1 11/2018

OTHER PUBLICATIONS

Ota, Ghost Cytometry, Jun. 15, 2018, Science 360, pp. 1246-1251 (Year: 2018).*

(Continued)

*Primary Examiner* — Charles Capozzi
*Assistant Examiner* — Alex Ramirez
(74) *Attorney, Agent, or Firm* — XSENSUS LLP

(57) ABSTRACT

A cell analysis device includes a determination target identifier extraction portion configured to extract a determination target identifier that is information indicating an identification substance associated with a determination target cell that is a cell of a determination target from a table indicating a corresponding relationship between the cell and the identification substance for each compartment with respect to compartments flowing along a flow path including the cell and the identification substance that is a substance associated with the cell, an identifier acquisition portion configured to acquire the identifier that is the information for identifying the identification substance included in the compartments flowing along the flow path, a determination portion configured to determine a compartment including the determination target cell among the compartments flowing along the flow path on the basis of the identifier acquired by the identifier acquisition portion and the determination target identifier extracted by the determination target iden- (Continued)

tifier extraction portion, and an output portion configured to output a determination result of the determination portion.

11 Claims, 33 Drawing Sheets

(51) Int. Cl.
*G01N 15/14* (2024.01)
*G01N 15/1492* (2024.01)
*G01N 33/58* (2006.01)

(52) U.S. Cl.
CPC ... *G01N 33/582* (2013.01); *G01N 2015/1006* (2013.01); *G01N 2015/1481* (2013.01)

(56) References Cited

OTHER PUBLICATIONS

Sarafraz-Yazdi, Anticancer peptide PNC-27 adopts an HDM-2 binding conformation and kills cancer cells by binding to HDM-2 in their membranes, Feb. 2, 2010, PNAS, pp. 1918-1923 (Year: 2010).*

International Search Report issued Jun. 22, 2021 in International Application No. PCT/JP2021/013937, 4 pages.

Evan Z. Macosko, et al., Highly parallel genome-wide expression profiling of individual cells using nanoliter droplets, Cell. Author manuscript, 161(5), May 21, 2015, 25 pages.

Anna Fornell, et al., An acoustofluidic platform for non-contact trapping of cell-laden hydrogel droplets compatible with optical microscopy, Biomicrofluidics 13, 044101, Jul. 11, 2019, 8 pages.

Maria Tenje, et al., Particle Manipulation Methods in Droplet Microfluidics, Analytical Chemistry, 90, Nov. 30, 2017, 10 pages.

Sadao Ota, et al., Ghost cytometry, Science, vol. 360, Jun. 15, 2018, 6 pages.

Hiroaki Adachi, et al., Use of Ghost Cytometry to Differentiate Cells with Similar Gross Morphologic Characteristics, Cytometry Part A, vol. 97A, Mar. 1, 2020, 8 pages.

* cited by examiner

| BEAD NUMBER | IDENTIFIER | | |
|---|---|---|---|
| | R | G | B |
| #1 | 3 | 3 | 3 |
| #2 | 3 | 3 | 2 |
| #3 | 3 | 3 | 1 |

| COMPARTMENT | CELL INFORMATION | IDENTIFIER | | |
|---|---|---|---|---|
| | | R | G | B |
| COMPARTMENT 1 | CELL IMAGE 1 | 3 | 3 | 3 |
| COMPARTMENT 2 | CELL IMAGE 2 | 3 | 3 | 2 |
| COMPARTMENT 3 | CELL IMAGE 3 | 3 | 3 | 1 |

| BEAD NUMBER | IMAGING INFORMATION | | | FIRST BARCODE SEQUENCE |
|---|---|---|---|---|
| | R | G | B | |
| #1 | 3 | 3 | 3 | ATGCATGC · · · |
| #2 | 3 | 3 | 2 | TGACTGAC · · · |
| #3 | 3 | 3 | 1 | GATCGATC · · · |

FIG. 31

| BEAD NUMBER | CELL | GENOME |
|---|---|---|
| #1 | CELL A | XXXXXXXX |
| #2 | CELL B | YYYYYYYY |
| #3 | CELL C | ZZZZZZZZ |

FIG. 33

| COMPARTMENT | CLASS OF CELL BASED ON CLASSIFICATION MODEL | CELL INFORMATION | GENOME-RELATED INFORMATION | IMAGING INFORMATION | | |
|---|---|---|---|---|---|---|
| | | | | R | G | B |
| COMPARTMENT 1 | RESPOND TO CERTAIN CHEMICAL | CELL IMAGE 1 | XXXXXXX | 3 | 3 | 3 |
| COMPARTMENT 2 | | CELL IMAGE 2 | YYYYYYYY | 3 | 3 | 2 |
| COMPARTMENT 3 | | CELL IMAGE 3 | ZZZZZZZZ | 3 | 3 | 1 |
| COMPARTMENT 4 | DOES NOT RESPOND TO CERTAIN CHEMICAL | CELL IMAGE 4 | VVVVVVV | 3 | 2 | 3 |
| COMPARTMENT 5 | | CELL IMAGE 5 | WWWWWWW | 3 | 2 | 2 |

CELL ANALYSIS DEVICE, CELL DETERMINATION METHOD, AND PROGRAM

TECHNICAL FIELD

The present invention relates to a cell analysis device, a cell determination method, and a program.

Priority is claimed on Japanese Patent Application No. 2020-065988, filed Apr. 1, 2020, the content of which is incorporated herein by reference.

BACKGROUND ART

Even within cells of the same type, it has become obvious that there is diversity in gene expression for each individual cell and there is a need to elucidate gene expression for each individual cell.

As a method of detecting transcription products derived from a certain cell, a method of obtaining data of genetic information of a cell using beads to which nucleic acids containing barcode sequences are linked and using sequencing technology is known (Patent Document 1).

On the other hand, imaging technology such as imaging cytometry is used to identify morphological information of cells. An image cell sorter having a function of sorting cells in imaging cytometry is known. Conventional image cell sorter technology has been implemented in a high-speed real-time process for high-content (for example, data of three- and two-dimensional images and the like) measurement information of cells.

CITATION LIST

Patent Literature

Patent Literature 1

PCT International Patent Publication No. WO 2015/166768

Non-Patent Literature

Non-Patent Literature 1

Evan Z. Macosko et al., Highly parallel genome-wide expression profiling of individual cells using nanoliter droplets, "Cell." May 21, 2015, 161, pp. 1201-1214

Non-Patent Literature 2

Anna Fornell, Carl Johannesson, Sean S. Searle, Axel Happstadius, Johan Nilsson, and Maria Tenje, An acoustofluidic platform for non-contact trapping of cell-laden hydrogel droplets compatible with optical microscopy, "Biomicrofluidics," Jul. 13, 2019, 13, 044101

Non-Patent Literature 3

Maria Tenje, Anna Fornell, Mathias Ohlin, and Johan Nilsson, Particle Manipulation Methods in Droplet Microfluidics, Analytical Chemistry, Nov. 30, 2017, 90, 1434-1443

SUMMARY OF INVENTION

Technical Problem

However, because an amount of information to be processed increases as the accuracy of measurement information increases, it is difficult to achieve both high accuracy and high speed. For example, high-speed and real-time separation is difficult because measurement information analysis using highly accurate deep learning is time-consuming. Therefore, there is a demand for fast and immediate cell separation on the basis of results of analyzing cell measurement information.

The present invention has been made in view of the above-described circumstances and an objective of the present invention is to provide a cell analysis device, a cell determination method, and a program capable of performing cell separation quickly and immediately on the basis of results of analyzing cell measurement information.

Solution to Problem

The present invention has been made to solve the above problems. According to an aspect of the present invention, there is provided a cell analysis device including: a determination target identifier extraction portion configured to extract a determination target identifier that is information indicating an identification substance associated with a determination target cell that is a cell of a determination target from a table indicating a corresponding relationship between the cell and the identification substance for each compartment with respect to compartments flowing along a flow path including the cell and the identification substance that is a substance associated with the cell; an identifier acquisition portion configured to acquire the identifier that is the information for identifying the identification substance included in the compartments flowing along the flow path; a determination portion configured to determine a compartment including the determination target cell among the compartments flowing along the flow path on the basis of the identifier acquired by the identifier acquisition portion and the determination target identifier extracted by the determination target identifier extraction portion; and an output portion configured to output a determination result of the determination portion.

Also, according to the aspect of the present invention, the identifier is information for optically identifying the identification substance.

Also, according to the aspect of the present invention, the identification substance is beads having imaging information that is information capable of being identified through imaging as the identifier.

Also, according to the aspect of the present invention, the imaging information is optical information about one or more of a visible light absorption spectrum, dispersion, a fluorescence intensity, scattering, and a Raman spectrum.

Also, according to the aspect of the present invention, the beads include a first bead to which a first barcode nucleic acid, which is a type of nucleic acid corresponding to the imaging information, is linked such that linkage is cleavable; and a second bead to which a plurality of genome-related nucleic acids corresponding to a cellular genome or its expression product or a plurality of second barcode nucleic acids, which are nucleic acids capable of hybridizing with the first barcode nucleic acid, are linked.

Also, according to the aspect of the present invention, the compartment is a gel, an identifier is a position of the identification substance within the compartment, and the identification substance is arranged at a position associated with the cell within the compartment.

Also, according to the aspect of the present invention, the identification substance includes a fluorescent molecule, and the identifier is a spectrum of the identification substance, a type of the fluorescent molecule, a concentration of fluorescent molecules, or a combination of types of fluorescent molecules.

Also, according to the aspect of the present invention, the table shows a corresponding relationship between cell information indicating the cell and the identification substance for each compartment, and the cell information is information obtained in high-content analysis.

Also, according to the aspect of the present invention, the identifier acquisition portion is able to acquire the identifier of the identification substance a plurality of times.

Also, according to the aspect of the present invention, a compartment determination result of the determination portion does not change every time the identifier is acquired when the identifier acquisition portion has acquired the identifier of the identification substance a plurality of times.

Also, according to the aspect of the present invention, the identifier acquisition portion acquires the identifier at timings different from each other with respect to the same compartment.

Also, according to an aspect of the present invention, there is provided a cell determination method including: a determination target identifier extraction process of extracting a determination target identifier that is information indicating an identification substance associated with a determination target cell that is a cell of a determination target from a table indicating a corresponding relationship between the cell and the identification substance for each compartment with respect to compartments flowing along a flow path including the cell and the identification substance that is a substance associated with the cell; an identifier acquisition process of acquiring the identifier that is the information for identifying the identification substance included in the compartments flowing along the flow path; a determination process of determining a compartment including the determination target cell among the compartments flowing along the flow path on the basis of the identifier acquired in the identifier acquisition process and the determination target identifier extracted in the determination target identifier extraction process; and an output process of outputting a determination result of the determination process.

Also, according to an aspect of the present invention, there is provided a program for allowing a computer to execute: a determination target identifier extraction step of extracting a determination target identifier that is information indicating an identification substance associated with a determination target cell that is a cell of a determination target from a table indicating a corresponding relationship between the cell and the identification substance for each compartment with respect to compartments flowing along a flow path including the cell and the identification substance that is a substance associated with the cell; an identifier acquisition step of acquiring the identifier that is the information for identifying the identification substance included in the compartments flowing along the flow path; a determination step of determining a compartment including the determination target cell among the compartments flowing along the flow path on the basis of the identifier acquired in the identifier acquisition step and the determination target identifier extracted in the determination target identifier extraction step; and an output step of outputting a determination result of the determination step.

Advantageous Effects of Invention

According to the present invention, cell separation can be performed quickly and immediately on the basis of results of analyzing cell measurement information.

BRIEF DESCRIPTION OF DRAWINGS

FIG. 31 is a diagram showing an example of information associated with the second beads according to the second embodiment of the present invention.

FIG. 33 is a diagram showing an example of a table according to the second embodiment of the present invention.

DESCRIPTION OF EMBODIMENTS

First Embodiment

Figure 1:
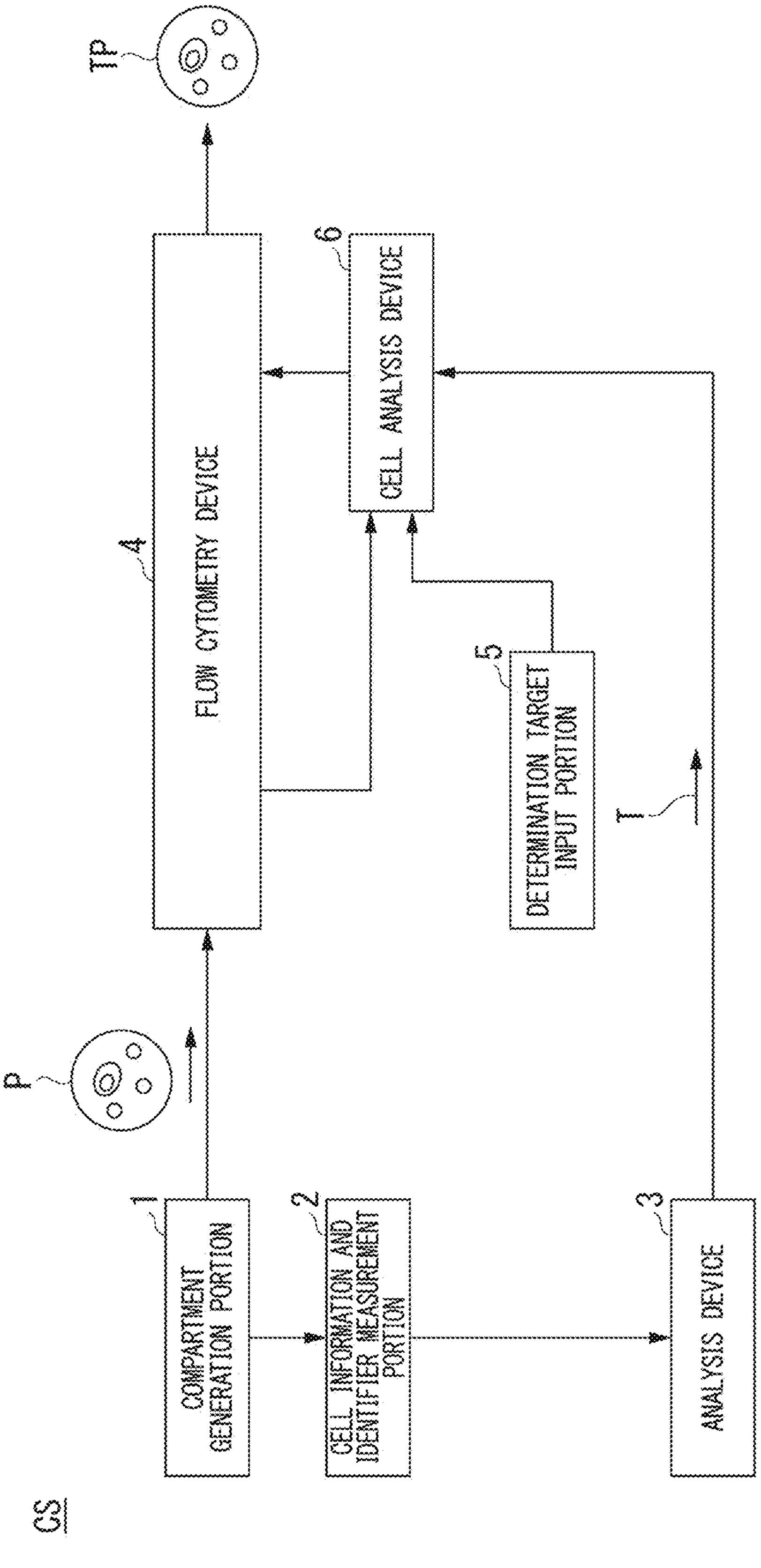
FIG. 1 is a diagram showing an example of a cell sorting system according to a first embodiment of the present invention.

Hereinafter, embodiments of the present invention will be described in detail with reference to the drawings. FIG. 1 is a diagram showing an example of a cell sorting system CS according to the present embodiment. The cell sorting system CS performs fast and immediate cell separation on the basis of a result of analyzing high-content measurement information of cells.

The cell sorting system CS includes a compartment generation portion 1, a cell information and identifier measurement portion 2, an analysis device 3, a flow cytometry device 4, a determination target input portion 5, and a cell analysis device 6.

The compartment generation portion 1 generates a compartment P. The compartment generation portion 1 is a microfluidic device. The compartment P includes a cell C and an identification substance MI that is a substance associated with the cell C.

The compartment is a space that is spatially separated from other liquids or nearby media. In other words, the compartment is a space compartmentalized from other liquids or nearby media. The compartment is preferably a certain volume of liquid or gel held in this space. The compartment is any one of droplets, gel particles, and wells. Compartments are, for example, aqueous droplets, oil droplets, gel particles of hydrogels such as agarose, collagen, and alginic acids, water-oil structures overlapping a plurality of non-mixing interfaces such as emulsions, wells of multiwell plates, and the like.

In the present embodiment, the compartment P is a droplet as an example. The identification substance MI is associated with a cell C using an identifier D. The identifier D is information for identifying the identification substance MI. In the present embodiment, the identifier D is, for example, information for optically identifying the identification substance MI. Here, optically identifying the identification substance MI includes identifying the identification substance MI through imaging and identifying the identification substance MI by analyzing a spectrum of light emitted from the identification substance MI. In the present embodiment, an example in which the identification substance MI is identified through imaging will be described and an example of spectral analysis of light emitted from the identification substance MI will be described below.

In the present embodiment, the identification substance MI is, for example, a bead B having imaging information IB that is information that can be identified through imaging. The imaging information IB is represented by a size, a color, and a dye density of the bead B as will be described below. That is, the identification substance MI is a bead B having a size, a color, and a dye concentration as the imaging information IB.

Figure 2:
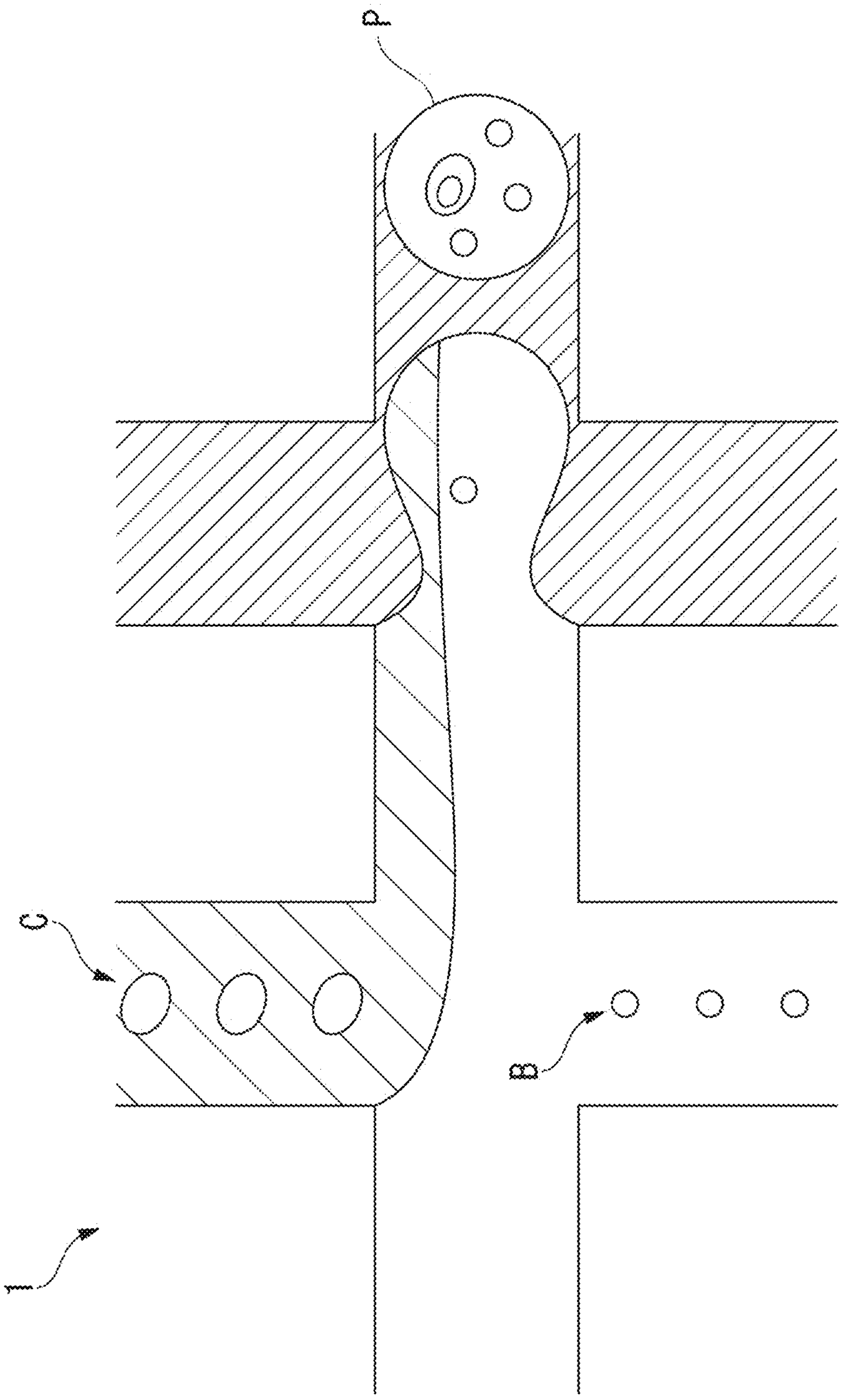
FIG. 2 is a diagram showing an example of a compartment generation portion according to the first embodiment of the present invention.

Here, the compartment generation portion 1 will be described with reference to FIG. 2. FIG. 2 is a diagram showing an example of the compartment generation portion 1 according to the present embodiment. The compartment generation portion 1 is the microfluidic device as described above and is a flow focusing device as an example. The compartment generation portion 1 generates a compartment P by allowing a fluid containing a cell C to merge with a fluid containing beads B to form a droplet.

The compartment generation portion 1 generates one compartment P by combining one cell among a plurality of types of cells C and a prescribed number of beads among a plurality of types of beads B. The number of types of cells Cis, for example, about $10^6$.

Figure 3:
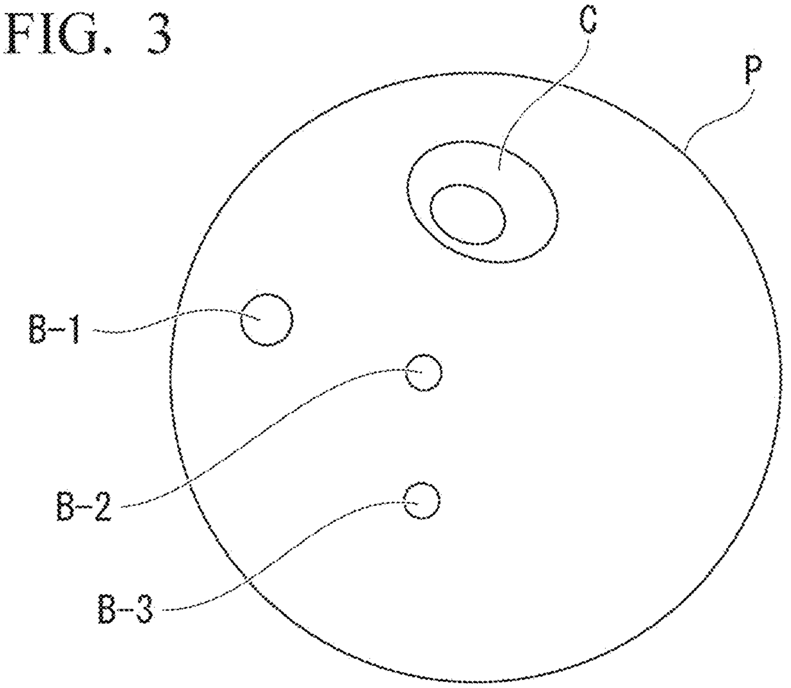
FIG. 3 is a diagram showing a first example of a compartment according to the first embodiment of the present invention.

Next, the compartment P will be described with reference to FIGS. 3 to 5. FIG. 3 is a diagram showing a first example of the compartment P according to the present embodiment. The compartment P includes one cell C per droplet and beads B. In the example shown in FIG. 3, the compartment P contains a plurality of beads B including a bead B-1, a bead B-2, and a bead B-3.

In the example shown in FIG. 3, the beads B and the cell C are included in the compartment P in a state in which the beads B are separated from the cell C within the compartment P. Also, a state in which the beads B and the cell C are included in the compartment P is not limited to this. In the compartment P, the beads B and the cell C may be included in the compartment P in a state in which the beads B are attached to the surface of the cell C. Also, in a state in which the beads B are included within the cell C within the compartment P, the beads B and the cell C may be included in the compartment P.

Figure 4:
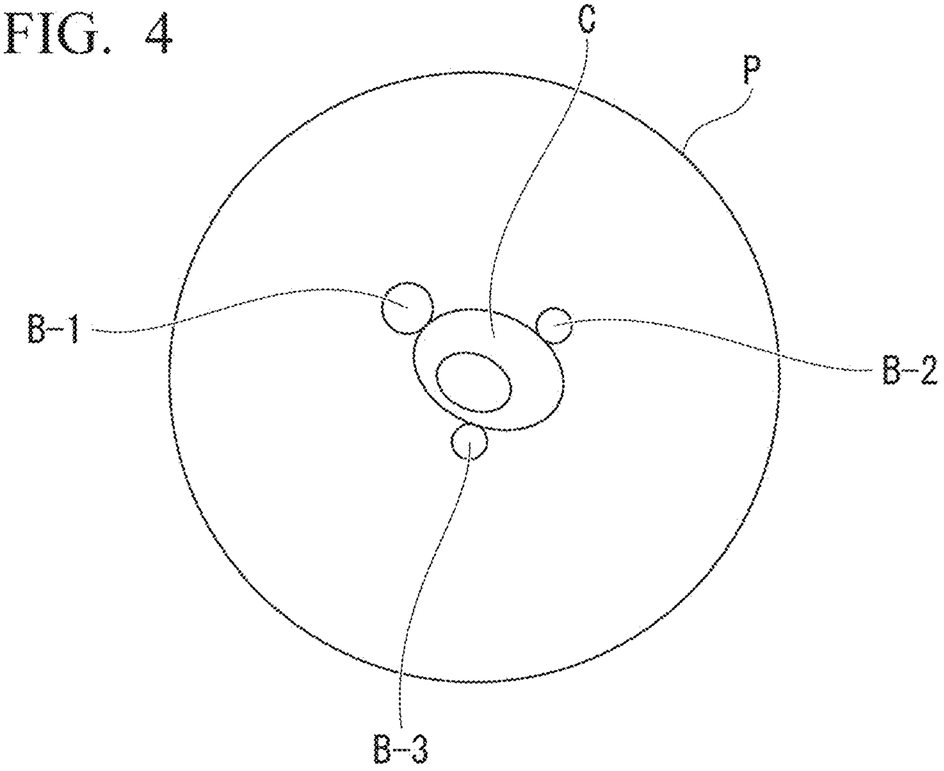
FIG. 4 is a diagram showing a second example of a compartment according to the first embodiment of the present invention.

As a second example of the compartment P, an example of the compartment P in which the beads B are attached to the surface of the cell C is shown in FIG. 4. As a third example of the compartment P, an example of the compartment P in which the beads B are included in the cell C is shown in FIG. 5.

The bead B has imaging information IB that is information capable of being identified through imaging. The imaging information IB of the bead B is, for example, a bead size, a fluorochrome color, a fluorochrome concentration, and the like. The imaging information IB may include optical information about one or more of a visible light absorption spectrum, dispersion, a fluorescence intensity, scattering, and a Raman spectrum in addition to the bead size, the fluorochrome color, and the fluorochrome concentration. Also, the imaging information IB may include optical information about one or more of a visible light absorption spectrum, dispersion, a fluorescence intensity, scattering, and a Raman spectrum instead of the bead size, the fluorochrome color, and the fluorochrome concentration.

When the imaging information IB of the bead B is a bead size, a fluorochrome color, and a fluorochrome concentration, there are three bead sizes (3, 7, and 11 μm), three fluorochrome colors (red, green, and blue), and six intensity levels based on the fluorochrome concentration. In this case, the number of types of beads B is $(6^3-1)\times3=645$.

It is only necessary for the number of beads B per compartment to be one or more. Preferably, the number of beads B per compartment is two or more such that the number of types of compartments that can be distinguished from each other increases. By including a plurality of beads B in the compartment P, the number of combinations of the imaging information IB of the beads B included within the compartment P can be increased by a combination of a small number of types of imaging information IB of the beads B. The number of types of compartments capable of being distinguished from each other can be increased according to the number of types associated with the number of combinations.

In the example shown in FIG. 3, three beads B are included within the compartment P, the number of types of combinations of the beads B is ${}_{645}C_3$, and a number of types of combinations greater in number than $10^6$ that is the number of types of cells C in the present embodiment can be obtained. That is, in the present embodiment, it is sufficient to associate the beads B with the types of cells C in the compartment P if three beads B are included within the compartment P.

The number of beads B included within the compartment P may be determined in accordance with the number of types of beads B and the number of types of cells C. In this case, for example, the number of beads B included within the compartment P is determined such that the number of combinations of types of beads B is greater than the number of types of cells C.

Although the beads B may have the same imaging information IB, it is preferable that the compartment P include a plurality of beads B having different types of imaging information IB.

The materials of the first bead B1 are not particularly limited, and include, for example, semiconductors such as quantum dots (semiconductor nanoparticles) made of semiconductor materials such as cadmium selenide (CdSe), zinc sulfide (ZnS), cadmium sulfide (CdS), zinc selenide (ZnSe), and zinc oxide (ZnO), inorganic substances such as heavy metals such as gold, hydrogels such as acrylamide, agarose, collagen, PhGDA, alginic acids, and polyethylene glycol (PEG)-based ones, resins such as polystyrene, polypropylene, and hydrophilic vinyl polymers, hydrophilic vinyl polymers with PEG or a derivative thereof, and the like. The first bead B1 is preferably a hydrogel.

Figures 5, 6:
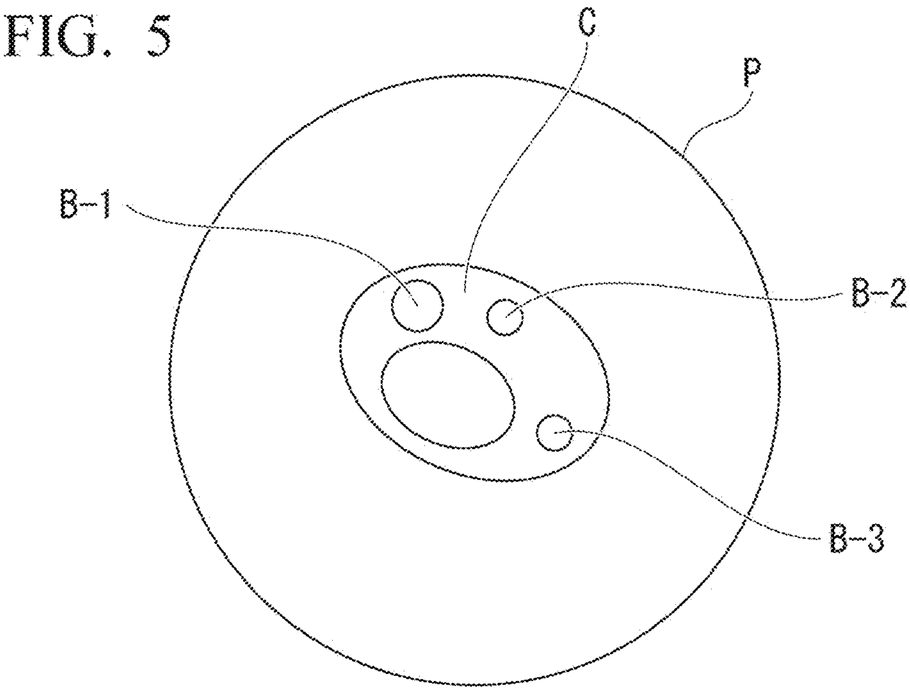
FIG. 5 is a diagram showing a third example of a compartment according to the first embodiment of the present invention.
FIG. 6 is a diagram showing an example of information associated with first beads according to the first embodiment of the present invention.

FIG. 6 is a diagram showing an example of imaging information IB associated with the first bead B1 according to the present embodiment. In FIG. 6, imaging information IB associated with beads B is shown for beads B with bead numbers #1, #2, and #3 as indicators of types of beads B.

As described above, the bead B has the imaging information IB. In FIG. 6, a fluorescence intensity level according to the fluorochrome concentration for each of the three colors (red, green, and blue) of the fluorochrome is indicated as an example of the imaging information IB.

Description of the cell sorting system CS will be continued with reference to FIG. 1 again.

The cell information and identifier measurement portion 2 measures the compartment P generated by the compartment generation portion 1. The cell information and identifier measurement portion 2 measures cell information IC for the cell C included in the compartment P. The cell information IC is information indicating the cell C. Also, the cell information and identifier measurement portion 2 measures the identifier D for the identification substance MI included in the compartment P. In the present embodiment, the cell information and identifier measurement portion 2 measures the imaging information IB as the identifier D for the identification substance MI included in the compartment P, as an example.

The cell information and identifier measurement portion 2 associates the measured cell information IC with the identifier D.

For example, the cell information and identifier measurement portion 2 associates the measured cell information IC with the imaging information IB.

Figures 7, 8:
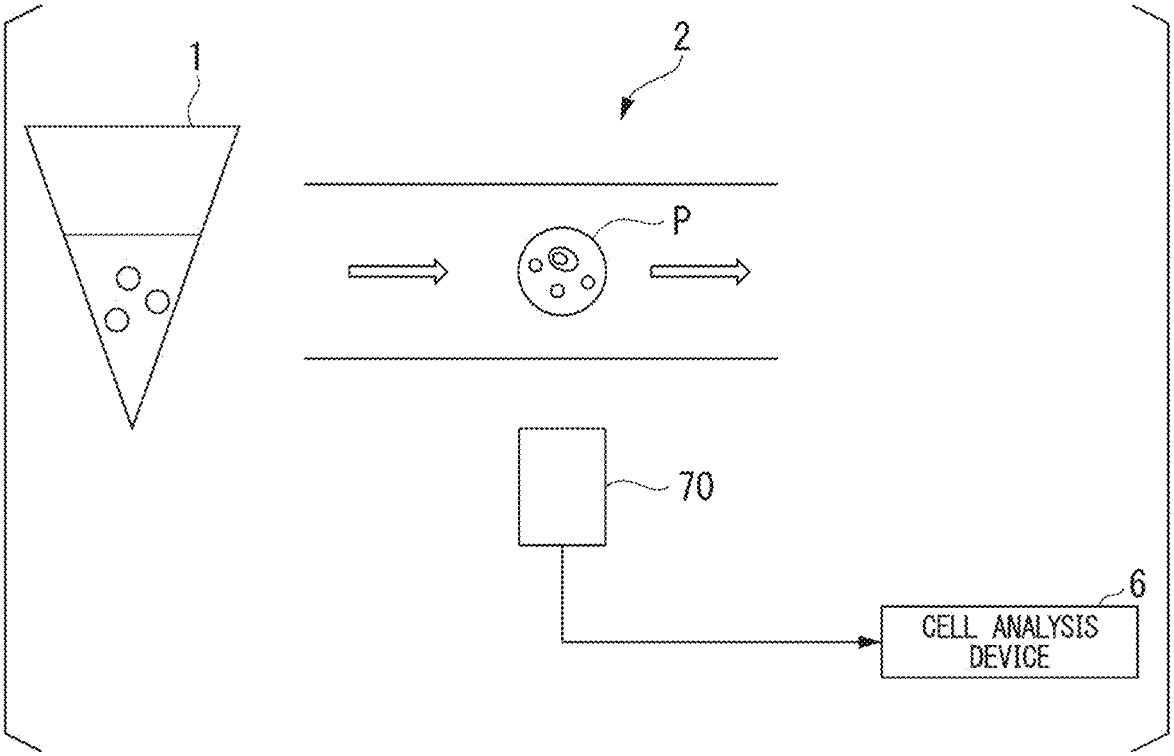
FIG. 7 is a diagram showing an example of cell information and identifier measurement according to the first embodiment of the present invention.
FIG. 8 is a diagram showing an example of a table according to the first embodiment of the present invention.

Here, a measurement process of the cell information and identifier measurement portion 2 will be described with reference to FIG. 7. FIG. 7 is a diagram showing an example in which the cell information IC and the identifier D are measured according to the present embodiment. The cell information and identifier measurement portion 2 is, for example, a microscope device or an imaging flow cytometry device.

The cell information and identifier measurement portion 2 measures both the cell information IC of the cell C included in the compartment P and the identifier D of the bead B. Here, the cell information and identifier measurement portion 2 observes the compartment P flowing along a flow path using, for example, fluorescence imaging. The cell information and identifier measurement portion 2 measures the cell information IC and the imaging information IB as the identifier D in an observation process using fluorescence imaging.

Although the imaging information IB of the beads B is not particularly limited as long as the imaging information IB of the beads B included in the compartment P can be distinguished from each other, the imaging information IB of the beads B may be imaging information included in the beads B themselves or imaging information assigned in a labeling process.

Here, the imaging is, for example, infrared spectroscopic imaging, Raman spectroscopic imaging, color imaging, fluorescence imaging, phase imaging, super-resolution imaging, or the like.

The imaging information IB is, for example, measurement information of one or more of a color, fluorescence, a size, a shape, electromagnetic waves, transmission, a phase, scattering, reflection, coherent Raman spectroscopy, infrared spectroscopy, Raman spectroscopy, or an absorption spectrum, in accordance with the imaging method.

The fluorescence can be obtained, for example, as an organic fluorescent molecule, a biological fluorescent molecule, a quantum dot, an inorganic substance such as a heavy metal, or a combination thereof.

Measurement information such as transmission, a phase, scattering, and reflection can be obtained as an organic substance, an inorganic substance, or a combination thereof with a refractive index or a color differing according to a concentration.

Absorption spectra and Raman spectroscopy can be obtained from organic substances, inorganic substances, or combinations thereof having absorption and Raman scattering spectra and having different absorption wavelength resistance.

Coherent Raman spectroscopy can be measured in, for example, a coherent anti-stokes Raman scattering (CARS) method, a stimulated Raman scattering (SRS) method, or the like.

Also, because the beads B and the cell C are spatially separated, the imaging information IB of the beads B can be measured without interfering with the cell information IC of the cell C.

Although the cell information IC is not particularly limited as long as it is possible to identify a feature of the cell C, the cell information IC is preferably information obtained in high-content analysis. The information obtained in high-content analysis in the present embodiment includes, for example, information including a plurality of parameters including an image of the cell C, morphological information of the cell C, reactions of the cell C to chemicals, sounds obtained from the cell C, measurement information of physical waves such as ultrasonic waves, measurement information of electromagnetic waves such as visible light and terahertz waves obtained from the cell C, and the like. Here, the image of the cell C can be obtained like the imaging information IB of the beads B.

An image of the cell C is, for example, an image based on measurement information of one or more of a color, fluorescence, a size, a shape, electromagnetic waves, transmission, a phase, scattering, reflection, coherent Raman spectroscopy, infrared spectroscopy, Raman spectroscopy, and an absorption spectrum.

The morphological information is, for example, information indicating morphology of the cell C such as sizes of a nucleus and a cytoplasm, the coarseness and density of cytoskeletons, a feature quantity of an internal structure, the uniformity of a membrane, a fluorescence intensity of each structure of the cell, molecular localization, and a positional relationship between molecules or observation targets.

After the compartment P is generated by the compartment generation portion 1, the cell information and identifier measurement portion 2 measures the cell information IC and the identifier D (the imaging information IB) for the cell C and the beads B included in the generated compartment P, respectively. Because the cell information and identifier measurement portion 2 performs the measurement after the compartment P is generated, the combination of the cell C and the bead B included in the compartment P can be confirmed.

Although an example in which the cell information and identifier measurement portion 2 measures the cell information IC and the identifier D (the imaging information IB) for the cell C and the beads B included in the generated compartment P after the compartment P is generated by the compartment generation portion 1 has been described as an example in the present embodiment, the present invention is not limited thereto.

The cell information and identifier measurement portion 2 may measure the cell information IC and the identifier D (the imaging information IB) for the cell C and the beads B before the compartment generation portion 1 generates the compartment P. When measurement is performed before the compartment P is generated, the cell information and identifier measurement portion 2 more accurately performs the measurement as compared with the case where the cell information IC and the identifier D (the imaging information IB) are measured in the state of the compartment P.

Also, the cell information and identifier measurement portion 2 may measure the cell information IC and the identifier D (the imaging information IB) both before and after the compartment generation portion 1 generates the compartment P.

Description of the cell sorting system CS will be continued with reference to FIG. 1 again.

The analysis device 3 generates a table T on the basis of the identifier D (the imaging information IB) and the cell information IC measured by the cell information and identifier measurement portion 2. The table Tis table information indicating the corresponding relationship between the cell C and the identification substance MI for each compartment P.

FIG. 8 shows an example of the table T according to the present embodiment. In the present embodiment, the table T shows the corresponding relationship between the cell information IC indicating the cell C and the identification substance MI for each compartment P. In the table T shown in FIG. 8, as an example, for each compartment P, the image of the cell C as the cell information IC and the imaging information IB as the identifier D are associated with each other.

The analysis device 3 outputs the generated table T to the cell analysis device 6. The analysis device 3 is, for example, a computer.

The flow cytometry device 4 sorts the determination target compartment TP including the determination target cell CT that is the determination target cell from among the plurality of compartments P supplied from the compartment generation portion 1. Here, the flow cytometry device 4 sorts the determination target compartment TP on the basis of a result of determining the determination target compartment TP in the cell analysis device 6.

The determination target input portion 5 receives an operation of selecting the determination target cell CT and outputs information indicating the determination target cell CT to the cell analysis device 6 on the basis of the received operation. The determination target input portion 5 is, for example, a mouse, a keyboard, a touch panel, or the like.

The cell analysis device 6 determines the determination target compartment TP on the basis of the table T generated by the analysis device 3 and the identifier D detected by the flow cytometry device 4. The cell analysis device 6 outputs a determination result to the flow cytometry device 4. The cell analysis device 6 is, for example, a computer.

Figure 9:
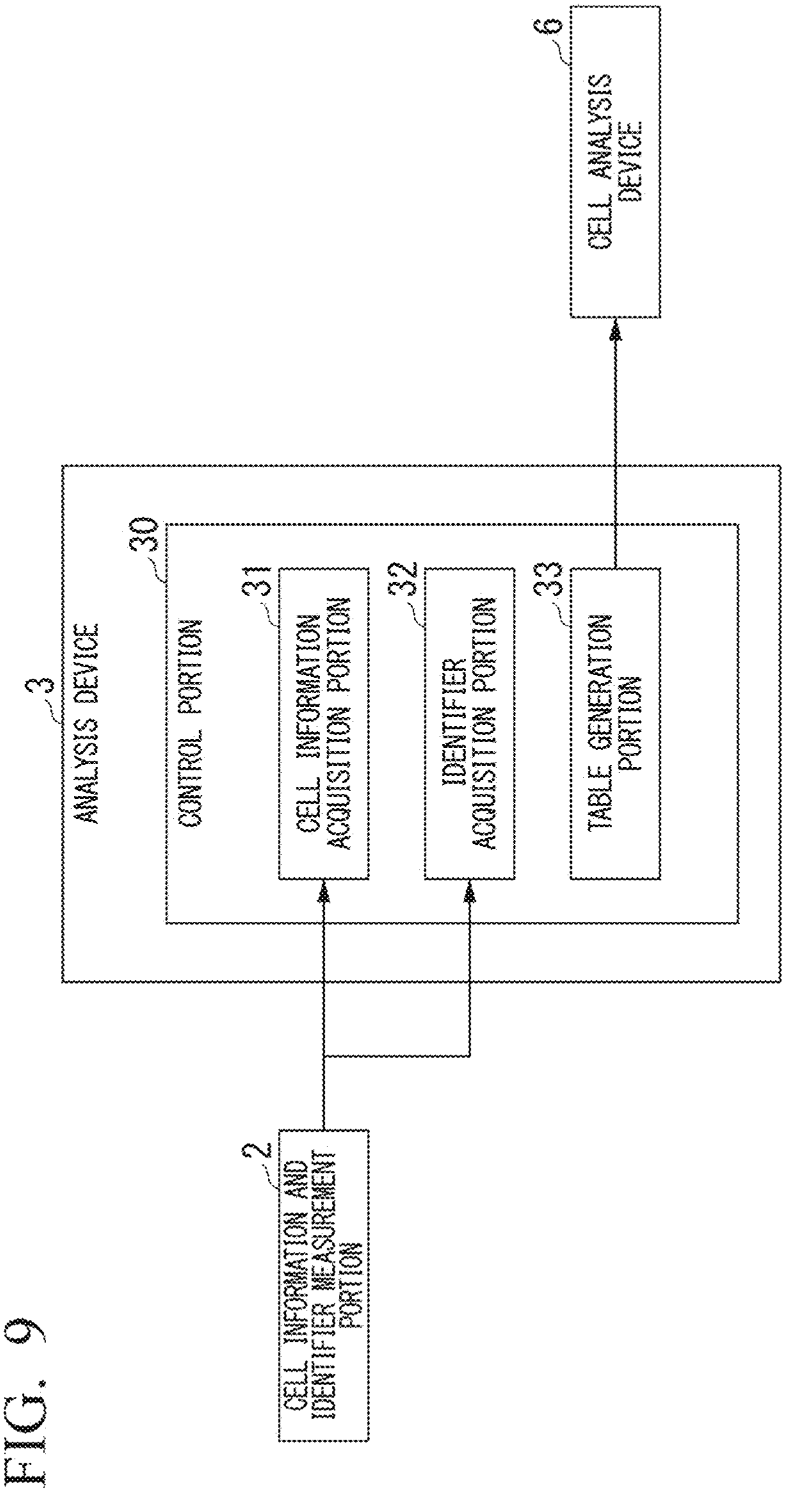
FIG. 9 is a diagram showing an example of a configuration of an analysis device according to the first embodiment of the present invention.

Here, a configuration of the analysis device 3 will be described with reference to FIG. 9. FIG. 9 is a diagram showing an example of the configuration of the analysis device 3 according to the present embodiment. The analysis device 3 includes a control portion 30. The control portion 30 includes a cell information acquisition portion 31, an identifier acquisition portion 32, and a table generation portion 33.

The control portion 30 is implemented by a central processing unit (CPU) and each of the cell information acquisition portion 31, the identifier acquisition portion 32, and the table generation portion 33 is a module implemented by the CPU reading a program from a read only memory (ROM) and executing a process.

The cell information acquisition portion 31 acquires the cell information IC output by the cell information and identifier measurement portion 2.

The identifier acquisition portion 32 acquires the identifier D (the imaging information IB) output by the cell information and identifier measurement portion 2.

The table generation portion 33 generates a table T on the basis of the cell information IC and the imaging information IB acquired by the identifier acquisition portion 32. The table generation portion 33 outputs the generated table T to the cell analysis device 6.

Figure 10:
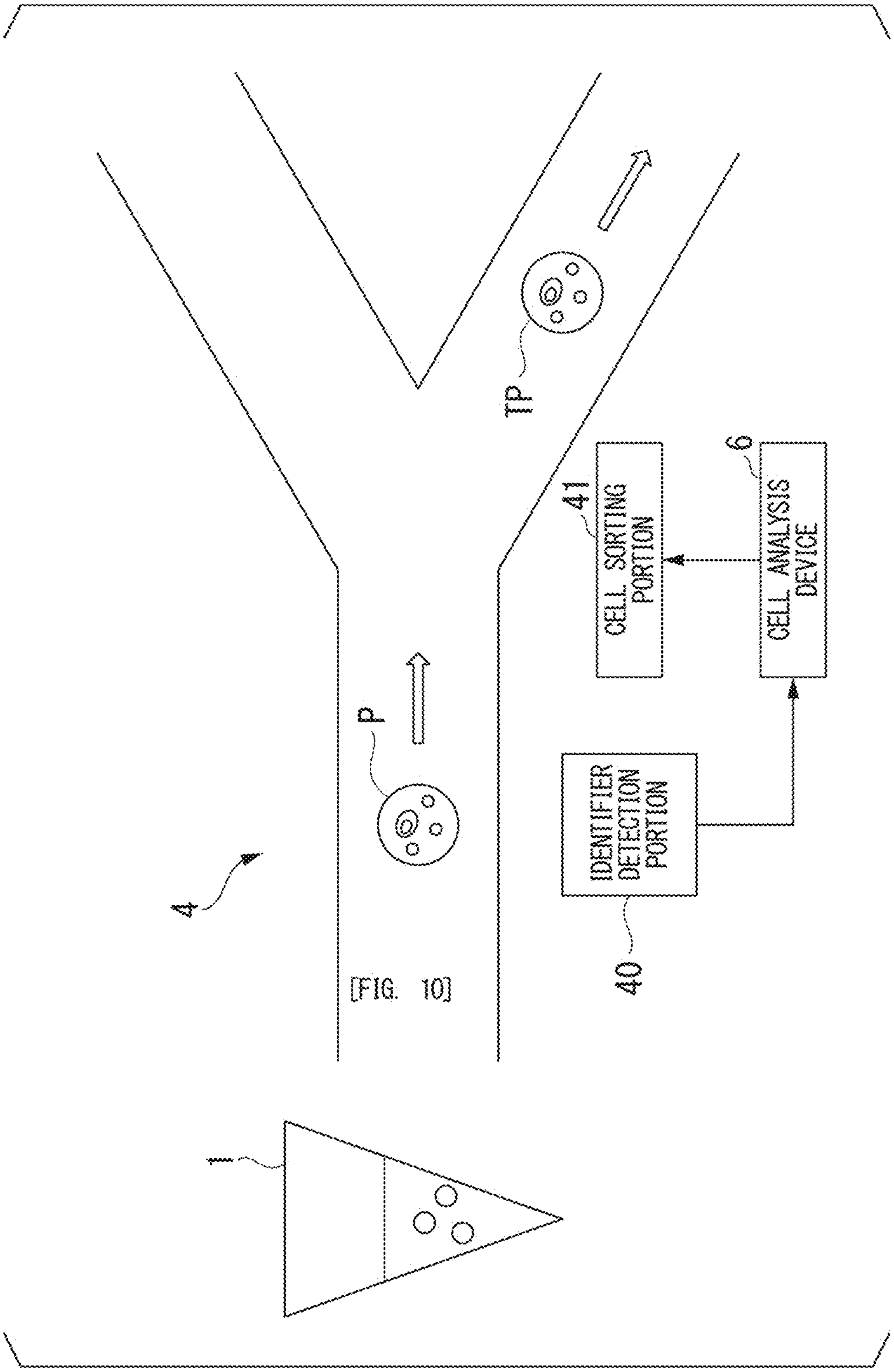
FIG. 10 is a diagram showing an example of a sorting process of a flow cytometry device according to the first embodiment of the present invention.

Next, a process of sorting the determination target compartment TP by the flow cytometry device 4 will be described with reference to FIG. 10. FIG. 10 is a diagram showing an example of a sorting process of the flow cytometry device 4 according to the present embodiment.

The flow cytometry device 4 includes an identifier detection portion 40 and a cell sorting portion 41.

The identifier detection portion 40 detects an identifier that is information about the identification substance MI included in the compartment P flowing along the flow path. In the present embodiment, the identifier detection portion 40 detects the imaging information IB of the bead B included in the compartment P as the identifier D.

The identifier detection portion 40 detects the imaging information IB of the beads B by observing the compartment P flowing along the flow path through, for example, fluorescence imaging. The identifier detection portion 40 is implemented, for example, by combining an array type detector or a line type detector with an optical element (for example, a dichroic mirror or a filter).

Also, the imaging in which the identifier detection portion 40 observes the compartment P flowing along the flow path is not limited to fluorescence imaging. The identifier detection portion 40 may use infrared spectroscopic imaging, Raman spectroscopic imaging, phase imaging, color imaging, or the like as imaging for observing the compartment P flowing along the flow path.

The cell sorting portion 41 sorts a determination target compartment TP from among a plurality of compartments P flowing along the flow path. The flow cytometry device 4 includes the cell sorting portion 41 and therefore functions as a cell sorter.

Figure 11:
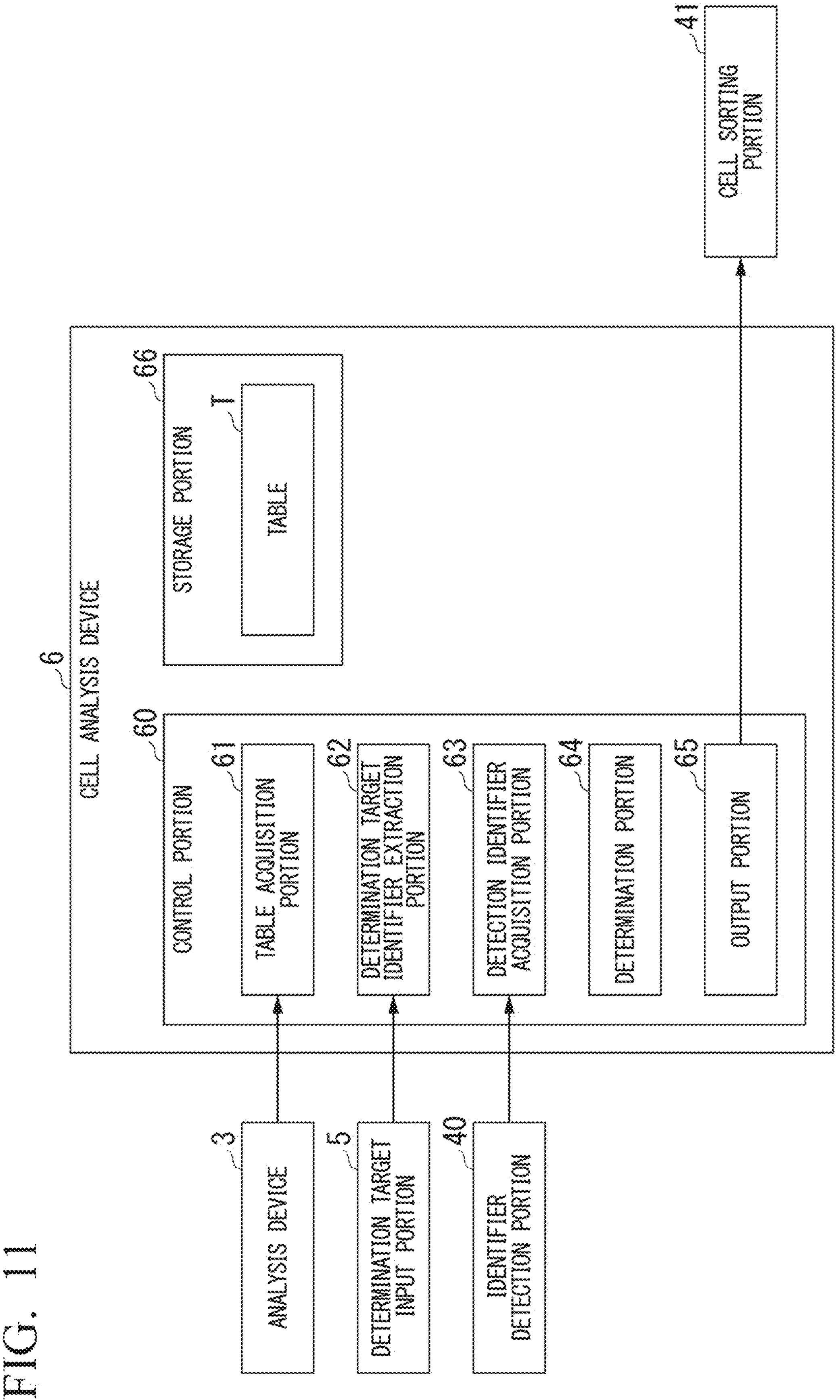
FIG. 11 is a diagram showing an example of a configuration of a cell analysis device according to the first embodiment of the present invention.

Next, a configuration of the cell analysis device 6 will be described with reference to FIG. 11. FIG. 9 is a diagram showing an example of the configuration of the cell analysis device 6 according to the present embodiment. The cell analysis device 6 includes a control portion 60 and a storage portion 66.

The control portion 60 includes a table acquisition portion 61, a determination target identifier extraction portion 62, a detection identifier acquisition portion 63, a determination portion 64, and an output portion 65. The control portion 60 is implemented by a CPU and each of the table acquisition portion 61, the determination target identifier extraction portion 62, the detection identifier acquisition portion 63, the determination portion 64, and the output portion 65 is a module implemented by the CPU reading a program from the ROM and executing a process.

The table acquisition portion 61 acquires the table T supplied from the analysis device 3.

The determination target identifier extraction portion 62 extracts the determination target identifier from the table T acquired by the table acquisition portion 61. A determination target identifier is information indicating an identification substance associated with the determination target cell CT received by the determination target input portion 5. In the present embodiment, the determination target identifier is the imaging information IB of the beads B included in the compartment P together with the determination target cell CT. This imaging information IB is referred to as determination target imaging information IBT.

The detection identifier acquisition portion 63 acquires the imaging information IB of the beads B included in the compartment P flowing along the flow path of the flow cytometry device 4. Here, the imaging information IB is detected by the identifier detection portion 40. The detection identifier acquisition portion 63 is an example of an identifier acquisition portion.

The determination portion 64 determines the determination target compartment TP from among compartments P flowing along the flow path of the flow cytometry device 4 on the basis of the imaging information IB acquired by the detection identifier acquisition portion 63 and the determination target imaging information IBT extracted by the determination target identifier extraction portion 62. The determination portion 64 supplies a determination result to the output portion 65.

The output portion 65 outputs the determination result of the determination portion 64 to the cell sorting portion 41 of the flow cytometry device 4.

The storage portion 66 stores the table T acquired by the table acquisition portion 61.

Figure 12:
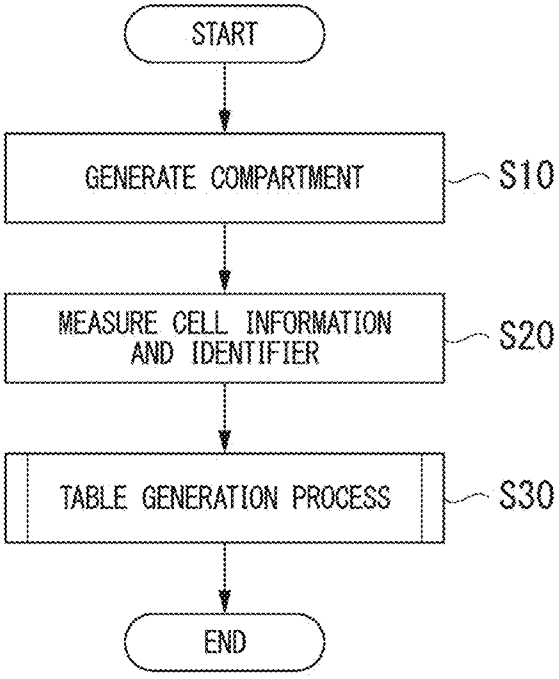
FIG. 12 is a diagram showing an example of a table preparation process according to the first embodiment of the present invention.

Here, a table preparation process, which is a process executed as preparation for generating the table T in the cell sorting system CS, will be described with reference to FIG. 12. FIG. 12 is a diagram showing an example of a table preparation process according to the present embodiment.

Step S10: The compartment generation portion 1 generates a compartment P. Here, the compartment generation portion 1 generates a plurality of types of compartments P by combining a plurality of types of cells C and a plurality of types of beads B. The compartment generation portion 1 supplies the generated compartments P to the cell information and identifier measurement portion 2.

Step S20: The cell information and identifier measurement portion 2 measures the cell information IC of the cell C included in the compartment P and the imaging information IB of the bead B included in the compartment P with respect to the compartments P generated by the compartment generation portion 1. The cell information and identifier measurement portion 2 supplies the measured cell information IC and the measured imaging information IB to the analysis device 3.

Step S30: The analysis device 3 executes a table generation process.

With this, the cell sorting system CS ends the table preparation process.

Figure 13:
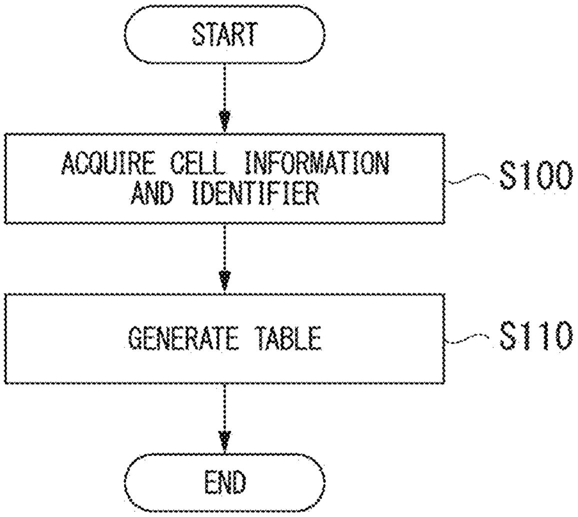
FIG. 13 is a diagram showing an example of a table generation process according to the first embodiment of the present invention.

Here, the table generation processing executed by the analysis device 3 will be described with reference to FIG. 13. FIG. 13 is a diagram showing an example of the table generation process according to the present embodiment.

Step S100: The cell information acquisition portion 31 acquires the cell information IC acquired by the cell information and identifier measurement portion 2. The cell information acquisition portion 31 supplies the acquired cell information IC to the table generation portion 33. On the other hand, the identifier acquisition portion 32 acquires the identifier D (the imaging information IB) acquired by the cell information and identifier measurement portion 2. The identifier acquisition portion 32 supplies the acquired identifier D (the imaging information IB) to the table generation portion 33.

Step S110: The table generation portion 33 generates a table T on the basis of the cell information IC acquired by the cell information acquisition portion 31 and the imaging information IB acquired by the identifier acquisition portion 32. The table generation portion 33 outputs the generated table T to the cell analysis device 6.

With this, the analysis device 3 ends the table generation process.

Figure 14:
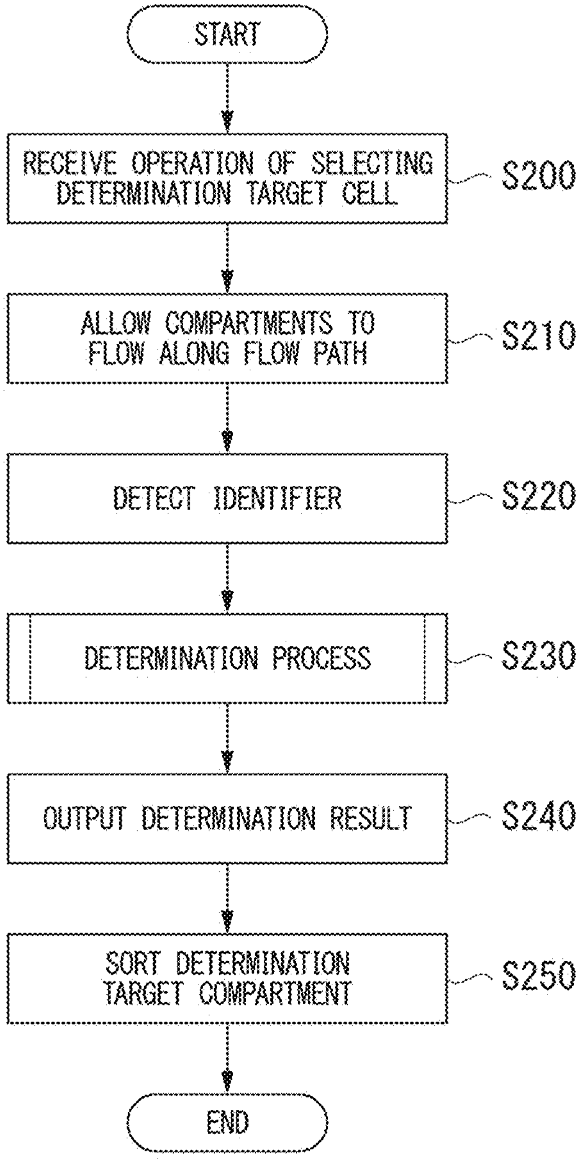
FIG. 14 is a diagram showing an example of a cell sorting process according to the first embodiment of the present invention.

Next, a cell sorting process, which is a process of sorting the determination target compartments TP in the cell sorting system CS, will be described with reference to FIG. 14. FIG. 14 is a diagram showing an example of the cell sorting process according to the present embodiment.

Step S200: The determination target input portion 5 receives an operation in which the user of the cell sorting system CS selects a determination target cell CT. The operation of selecting the determination target cell CT is performed using a mouse, a keyboard, a touch panel, or the like. The determination target input portion 5 outputs information indicating the determination target cell CT to the cell analysis device 6 on the basis of the received operation.

Step S210: The flow cytometry device 4 takes in a plurality of types of compartments P supplied from the compartment generation portion 1 and allows the plurality of types of compartments P to flow along the flow path.

Step S220: The identifier detection portion 40 detects the identifier D (the imaging information IB) of the first bead B1 included in the compartment P flowing along the flow path. The identifier detection portion 40 supplies the detected identifier D (the imaging information IB) to the determination portion 64.

Step S230: The cell analysis device 6 executes a determination process of determining the determination target compartment TP. Details of the determination process will be described below with reference to FIG. 15. The cell analysis device 6 supplies a result of the determination process to the cell sorting portion 41 of the flow cytometry device 4. Here, the result of the determination process is information indicating whether or not a compartment P, which is a determination target, among the compartments P flowing along the flow path of the flow cytometry device 4 is a determination target compartment TP.

Step S240: The output portion 65 outputs the result of the determination process of the determination portion 64 to the cell sorting portion 41 of the flow cytometry device 4.

Step S250: The cell sorting portion 41 sorts the determination target compartment TP from among the plurality of compartments P flowing along the flow path on the basis of the determination result of the cell analysis device 6. When the determination result of the cell analysis device 6 indicates that the compartment P, which is the determination target, is the determination target compartment TP, the cell sorting portion 41 sorts the compartment P that is the determination target.

With this, the cell sorting system CS ends the cell sorting process.

Here, the determination process of the cell analysis device 6 will be described with reference to FIG. 15. FIG. 13 is a diagram showing an example of the determination process according to the present embodiment.

Step S300: The table acquisition portion 61 acquires the table T supplied from the analysis device 3. The table acquisition portion 61 stores the acquired table T in the storage portion 66. Also, the table acquisition portion 61 may directly supply the acquired table T to the determination portion 64.

Step S310: The determination target identifier extraction portion 62 extracts the determination target identifier indicating the identification substance associated with the determination target cell CT received by the determination target input portion 5 from the table T acquired by the table acquisition portion 61. In the present embodiment, the determination target identifier extraction portion 62 extracts a determination target imaging information IBT from the table T. The determination target identifier extraction portion 62 supplies the extracted determination target imaging information IBT to the determination portion 64.

That is, the determination target identifier extraction portion 62 extracts a determination target identifier, which is information indicating the identification substance MI associated with the determination target cell CT that is a cell of a determination target, from the table T showing the corresponding relationship between the cell C and the identification substance MI for each compartment P with respect to the compartments P flowing along the flow path including the cell C and the identification substance MI that is the substance associated with the cell C.

Step S320: The detection identifier acquisition portion 63 acquires the identifier D (the imaging information IB) of the first bead B1 detected by the identifier detection portion 40. That is, the detection identifier acquisition portion 63 acquires the identifier D that is information for identifying the identification substance MI included in the compartment P flowing along the flow path.

Step S330: The determination portion 64 determines the determination target compartment TP from among the compartments P flowing along the flow path of the flow cytometry device 4 on the basis of the identifier D (the imaging information IB) acquired by the detection identifier acquisition portion 63 and the determination target imaging information IBT extracted by the determination target identifier extraction portion 62.

That is, the determination portion 64 determines the compartment P including the determination target cell CT from among the compartments P flowing along the flow path on the basis of the identifier acquired by the identifier acquisition portion and the determination target identifier extracted by the determination target identifier extraction portion 62.

With this, the cell analysis device 6 ends the determination process.

Although an example in which the cell analysis device 6 outputs a result of the determination process to the cell sorting portion 41 of the flow cytometry device 4 and the cell sorting portion 41 isolates the determination target cell CT has been described in the present embodiment, the present invention is not limited thereto. The result of the determination process of the cell analysis device 6 may be used for adding a chemical to the determination target cell CT flowing along the flow path in addition to the sorting of the cell.

The flow cytometry device 4 includes a chemical addition portion when the result of the determination process of the cell analysis device 6 is used for adding a chemical. The output portion 65 outputs the determination result of the determination portion 64 to the chemical addition portion of the flow cytometry device 4. The chemical addition portion adds a prescribed chemical to the determination target cell CT included in the determination target compartment TP among the plurality of compartments P flowing along the flow path on the basis of the determination result of the cell analysis device 6.

Although an example in which the table T is generated in the analysis device 3 within the cell sorting system CS has been described in the present embodiment, the present invention is not limited thereto. The table T may be generated by the cell analysis device 6 or generated by a device outside of the cell sorting system CS.

As described above, the cell analysis device 6 according to the present embodiment includes the determination target identifier extraction portion 62, the identifier acquisition portion (the detection identifier acquisition portion 63 in the present example), and the determination portion 64.

The determination target identifier extraction portion 62 extracts a determination target identifier (the determination target imaging information IBT in the present example) that is information indicating the identification substance MI (the first bead B1 in the present example) associated with a determination target cell CT that is a cell of a determination target from the table T indicating a corresponding relationship between the cell C and the identification substance MI (the first bead B1 in the present example) for each compartment P with respect to compartments P flowing along a flow path including the cell C and the identification substance MI (the first bead B1 in the present example) that is a substance associated with the cell C.

The identifier acquisition portion (the detection identifier acquisition portion 63 in the present example) acquires the identifier (the imaging information IB in the present example) that is the information for identifying the identification substance MI (the first bead B1 in the present example) included in the compartments P flowing along the flow path (the flow path of the flow cytometry device 4 in the present example).

The determination portion 64 determines a compartment (the determination target compartment TP in the present example) including the determination target cell CT from among the compartments P flowing along the flow path (the flow path of the flow cytometry device 4 in the present example) on the basis of the identifier (the imaging information IB in the present example) acquired by the identifier acquisition portion (the detection identifier acquisition portion 63 in the present example) and the determination target identifier (the determination target imaging information IBT in the present example) extracted by the determination target identifier extraction portion 62.

The output portion 65 outputs a determination result of the determination portion 64 (a result of the determination process in step S230 in the present example).

According to this configuration, because the cell analysis device 6 according to the present embodiment can determine the compartment (the determination target compartment TP in the present example) including the determination target cell CT on the basis of the determination target identifier extracted from the table T indicating the corresponding relationship between the cell information IC and the identification substance MI (the first bead B1 in the present example) for each compartment P, it is possible to separate cells quickly and immediately on the basis of a result of analyzing the cell measurement information.

As described above, in the cell analysis device 6 according to the present embodiment, the cell information IC is measured and analyzed in advance as cell measurement information without being measured in real time. Here, the cell information IC requires time for measurement in accordance with the accuracy of the information. In the cell analysis device 6, it is possible to determine the cell C on the basis of the identification substance MI associated with the cell C instead of determining the cell C on the basis of the cell information IC that requires time for measurement. Here, the cell information IC and the identification substance MI are associated in the table T showing the corresponding relationship for each compartment P. Thus, the cell analysis device 6 can perform fast and immediate cell separation on the basis of the result of analyzing the cell measurement information. Here, if cell separation can be performed quickly and immediately, this indicates that the cell is determined and separated quickly and immediately when the cell flows along the flow path of the flow cytometry device. In the cell analysis device 6 according to the present embodiment, the cell C can be separated on the basis of the cell information IC, which is information larger than that of the identification substance MI, by quickly and immediately determining the identification substance MI.

Also, in the cell analysis device 6 according to the present embodiment, even if the shape of the cell changes from a point in time when the cell information IC is measured, the cell C can be determined on the basis of the identifier D of the identification substance MI, such that the determination accuracy can be improved as compared to the conventional case where the cell information IC is measured in real time and the cell C is determined.

Conventionally, bead imaging information is used to associate a cell with the cell information of the cell. For example, the bead imaging information is used to associate cells whose cell information is measured at different timings or to associate cells whose cell information is measured by different measuring devices. Thus, conventionally, it is unnecessary to use a cell determination result immediately. On the other hand, in the cell analysis device 6 according to the present embodiment, when the imaging information IB of the bead B is used to determine the cell C, the determination result is output to another device (the flow cytometry device 4 in the present example) and is used immediately in this other device.

Also, in the cell analysis device 6 according to the present embodiment, the identifier D is information for optically identifying the identification substance MI.

According to this configuration, the cell analysis device 6 according to the present embodiment can perform a determination process without destroying the determination target cell CT because it is possible to determine the compartment (the determination target compartment TP in the present example) including the determination target cell CT by optically identifying the identification substance MI.

Also, in the cell analysis device 6 according to the present embodiment, the identification substance MI is a bead B having imaging information IB, which is information capable of being identified through imaging, as the identifier D.

According to this configuration, the cell analysis device 6 according to the present embodiment can perform a determination process without destroying the determination target cell CT using imaging because it is possible to determine the compartment (the determination target compartment TP in the present example) including the determination target cell CT by identifying the identification substance MI through imaging.

Also, in the cell analysis device 6 according to the present embodiment, the imaging information IB is optical information about one or more of a visible light absorption spectrum, dispersion, a fluorescence intensity, scattering, and a Raman spectrum.

According to this configuration, in the cell analysis device 6 according to the present embodiment, it is possible to increase the number of types of compartments capable of being identified on the basis of optical information because it is possible to increase the number of types of beads B in accordance with a combination of optical information about one or more of a visible light absorption spectrum, dispersion, a fluorescence intensity, scattering, and a Raman spectrum.

Also, in the cell analysis device 6 according to the present embodiment, the table T shows the corresponding relationship between the cell information IC indicating the cell C and the identification substance MI for each compartment P and the cell information IC is information obtained in high-content analysis.

According to this configuration, because the cell analysis device 6 according to the present embodiment can use information obtained in high-content analysis as the cell information IC, fast and immediate cell separation is enabled on the basis of information obtained in the high-content analysis for the cell.

Modified Example 1

In the first embodiment, an example in which the compartment is a droplet has been described. As the modified example, the measurement of imaging information when the compartment is a gel will be described. The compartment generation portion according to Modified Example 1 is referred to as a compartment generation portion 1*a*.

Figure 16:
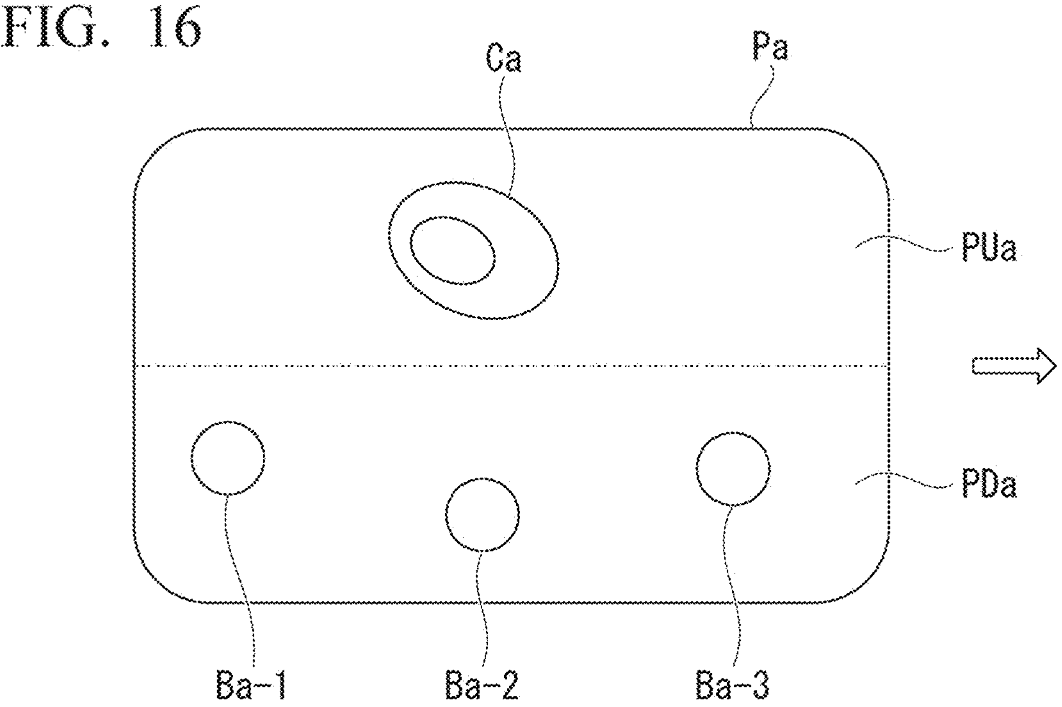
FIG. 16 is a diagram showing an example of a compartment according to Modified Example 1 of the first embodiment of the present invention.

FIG. 16 is a diagram showing an example of a compartment Pa according to the present modified example. The compartment Pa is a gel. The compartment Pa is divided into two parts in a direction perpendicular to a flow velocity direction of the flow path. These two parts are referred to as an upper part PUa and a lower part PDa. As an example, a cell Ca is arranged in the upper part PUa and a bead Ba is arranged in the lower part PDa.

The bead Ba is arranged at a position associated with the cell Ca in the lower part PDa. That is, in the compartment Pa, an identification substance MIa is arranged at a position associated with the cell Ca within the compartment Pa, which is a gel. Here, an identifier Da, which is information for identifying the identification substance MIa, is a position of the identification substance MIa within the compartment Pa.

Because the cell Ca or the bead Ba is confined within a gel particle and does not move or rotate in the compartment Pa, stable imaging is enabled. In FIG. 16, a bead Ba-1, a bead Ba-2, and a bead Ba-3 are shown as examples of the bead Ba.

In Modified Example 1, it is only necessary to identify the position of the bead Ba within the compartment Pa and it is unnecessary to identify the type of bead Ba. Therefore, any type of bead Ba may be used as long as the bead Ba has imaging information that can be identified through imaging.

For example, types of beads Ba may be identical and positions of a plurality of beads Ba within the compartment Pa may be different for each compartment Pa. Beads Ba of the same type indicate that they have the same imaging information IB.

Also, the identification substance MIa may be identified using the type of bead Ba in addition to the position of the identification substance MIa within the compartment Pa. For example, the identification substance MIa may be identified using optical information of one or more of a visible light absorption spectrum, dispersion, a fluorescence intensity, scattering, and a Raman spectrum of the identification substance MIa in addition to the position within the compartment Pa. That is, the identifier Da may include the above-described imaging information IB in addition to the position of the identification substance MIa within the compartment Pa.

Also, when the identification substance MIa is identified using the type in addition to the position within the compartment Pa, a relative positional relationship within the compartment Pa of the beads Ba of different types may be used as the identifier Da. Here, the relative positional relationship is, for example, a permutation in which the beads Ba of different types are arranged within the compartment Pa. This permutation is the order in which the beads Ba of different types are arranged within the compartment Pa in the flow velocity direction when the compartment Pa flows along the flow path.

Figure 17:
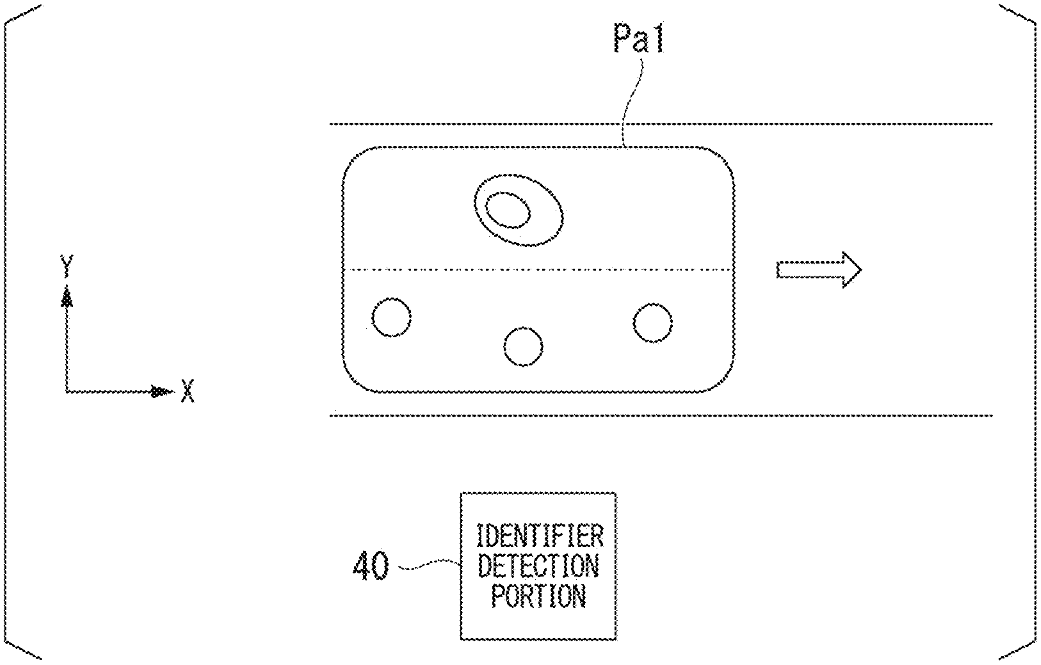
FIG. 17 is a diagram showing an example of a compartment moving along a flow path according to Modified Example 1 of the first embodiment of the present invention.

FIG. 17 is a diagram showing an example of the compartment Pa1 moving along the flow path according to the present modified example. This flow path is the flow path of the flow cytometry device 4. In FIG. 17, the compartment Pa1 is moving along the flow path as an example of the compartment Pa that is the gel. The X-axis is taken in the flow velocity direction in the flow path and the Y-axis is taken in a direction perpendicular to this flow velocity direction.

The identifier detection portion 40 performs imaging by imaging the compartment Pa1, for example, in the +Y-axis direction. Here, the identifier detection portion 40 images the lower part PDa in which the beads Ba are arranged in the compartment Pa1. For stable imaging, the compartment Pa1 preferably does not rotate in the flow velocity direction. Therefore, for stable imaging, a width of the compartment Pa1 in the Y-axis direction is preferably approximately the same as a width of the flow path in the Y-axis direction.

Figure 18:
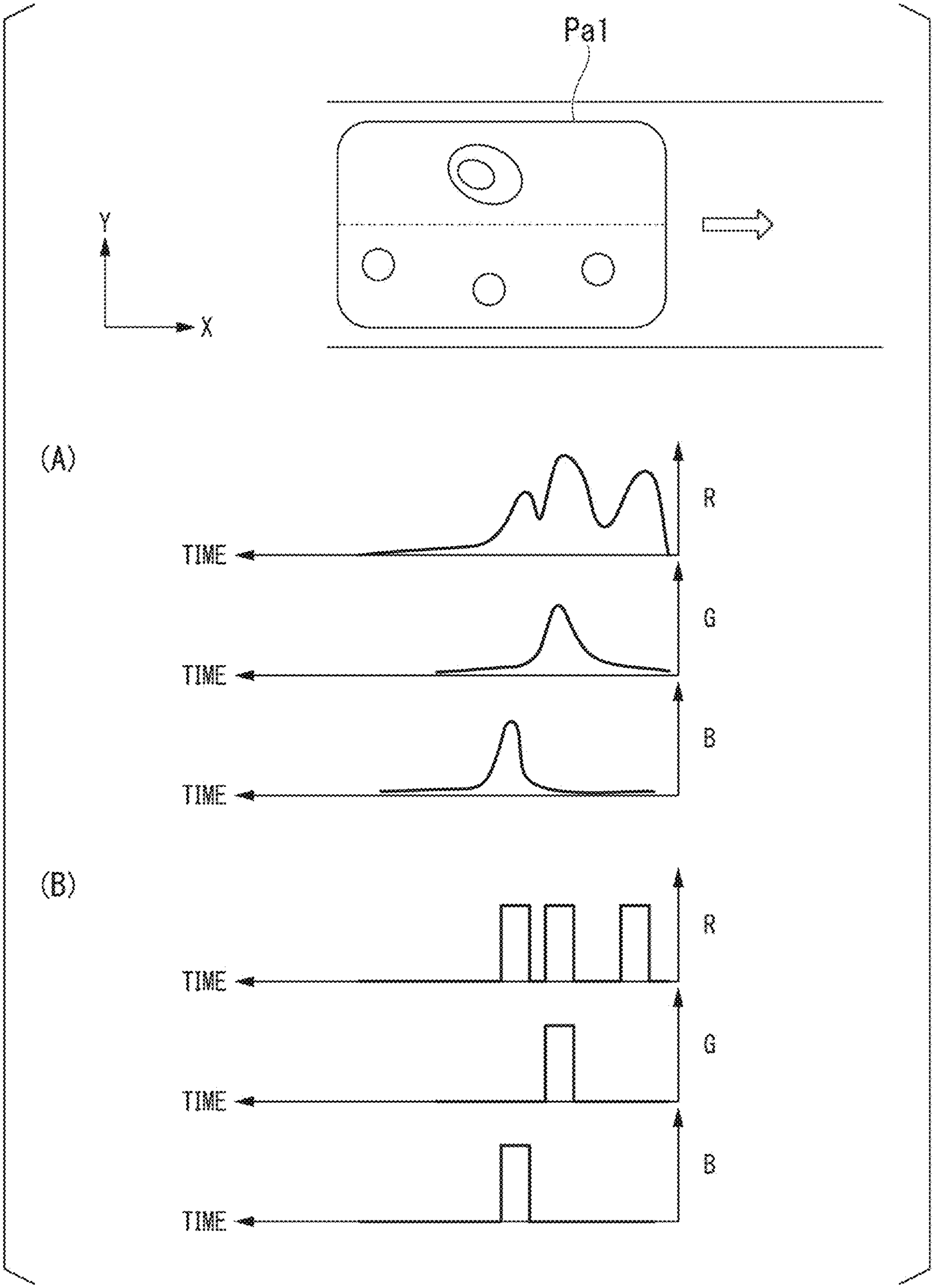
FIG. 18 is a diagram showing an example of results of measuring imaging information according to Modified Example 1 of the first embodiment of the present invention.

FIG. 18 is a diagram showing an example of a result of measuring the imaging information IB according to the present modified example. FIG. 18(A) shows time-series changes in intensity level measurement results based on fluorochrome concentrations in the bead Ba included in the compartment Pa1 for colors of red, green, and blue fluorochromes. Because the compartment Pa1 is imaged from the Y-axis direction, the intensity level based on the fluorochrome concentration of the bead Ba is measured as a sum (integral) value in the Y-axis direction. That is, in the present example, information of the spatial distribution of the beads B in the compartment Pa1 in the Y-axis direction is not reflected in measurement results.

FIG. 18(B) shows time-series changes obtained by binarizing the time-series changes in the measurement results of FIG. 18(A) on the basis of a prescribed threshold value. The time-series changes in the measurement results are the measurement results for the entire length of the compartment Pa1 in the X-axis direction. A length of the compartment Pa1 in the X-axis direction corresponds to the number of pixels in a direction corresponding to the X-axis direction of the image of the compartment Pa1.

As described above, in the compartment Pa1, the beads Ba are arranged at positions associated with the cell Ca. Thus, $(2^3)^{sp}$ combinations can be expressed by obtaining the binarized time-series changes in the measurement results for each color. Here, #P is the number of pixels in the direction corresponding to the X-axis direction of the image of the compartment Pa1.

As described above, in the cell analysis device according to the present modified example, the compartment Pa is a gel, the identifier Da is a position of the identification substance MIa within the compartment Pa, and the identification substance MIa is arranged at a position associated with the cell Ca within the compartment Pa.

According to this configuration, because the cell analysis device according to the present modified example can determine the cell Ca on the basis of the arrangement of the identification substance MIa within the compartment Pa, the number of types of identification substances MIa required for the determination can be reduced. Here, the reduction in the number of types of identification substances MIa indicates that the number of identification substances MIa can be reduced as compared to the case where no identification substance MIa is arranged at positions associated with the cell Ca within the compartment Pa.

Modified Example 2

As Modified Example 2 of the present embodiment, when the identifier is a position of the identification substance within the compartment as in the above-described Modified Example 1, an example in which the accuracy of detection of the identifier is improved by arranging the identification substances in one or two lines will be described. In the following description, the identifier as the arrangement of the identification substance in the present modified example is also referred to as a spatial barcode.

Figure 19:
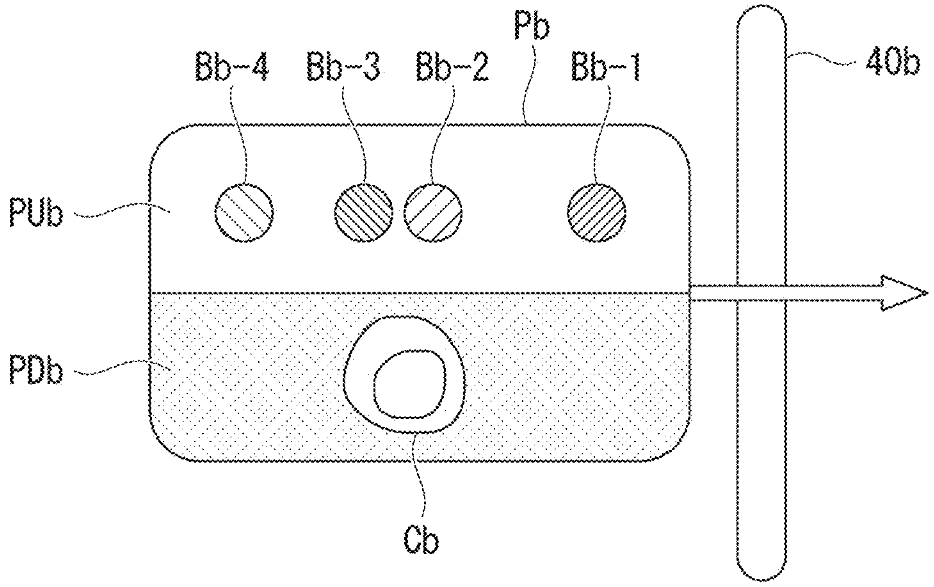
FIG. 19 is a diagram showing an example of a compartment according to Modified Example 2 of the first embodiment of the present invention.

FIG. 19 is a diagram showing an example of a compartment Pb according to the present modified example. As in Modified Example 1, the compartment Pb is a gel and is divided into two parts that are an upper part PUb and a lower part PDb in a direction perpendicular to a flow velocity direction of a flow path. As an example, beads Bb are arranged in the upper part PUb and a cell Cb is arranged in the lower part PDb. In FIG. 19, beads Bb1 to Bb4 are arranged as the beads Bb.

The beads Bb are arranged at positions associated with the cell Ch in the upper part PUb. Here, the beads Bb are arranged in a line in the flow velocity direction of the flow path as shown in FIG. 19. That is, the beads Bb are arranged within the compartment Pb without overlapping each other in the flow velocity direction.

The beads Bb may be identified using optical information such as, for example, a visible light absorption spectrum (i.e., a color), in addition to their positions within compartment Pb. In this case, the identifier includes a spatial barcode and optical information.

The line detector 40*b* is an example of an identifier detection portion and detects beads Bb moving in the flow velocity direction. The line detector 40*b* detects an arrangement of the beads Bb within the compartment Pb and a color of the beads Bb by detecting the beads Bb. That is, the line detector 40*b* detects spatial barcode information and optical information. When the line detector 40*b* detects light from the beads Bb here, the detected light is split. The line detector 40*b* detects an RGB luminance distribution within its own device using the fact that the movement direction of the split light differs according to the color. The line detector 40*b* detects the color of the beads Bb on the basis of the detected RGB luminance distribution.

Figure 20:
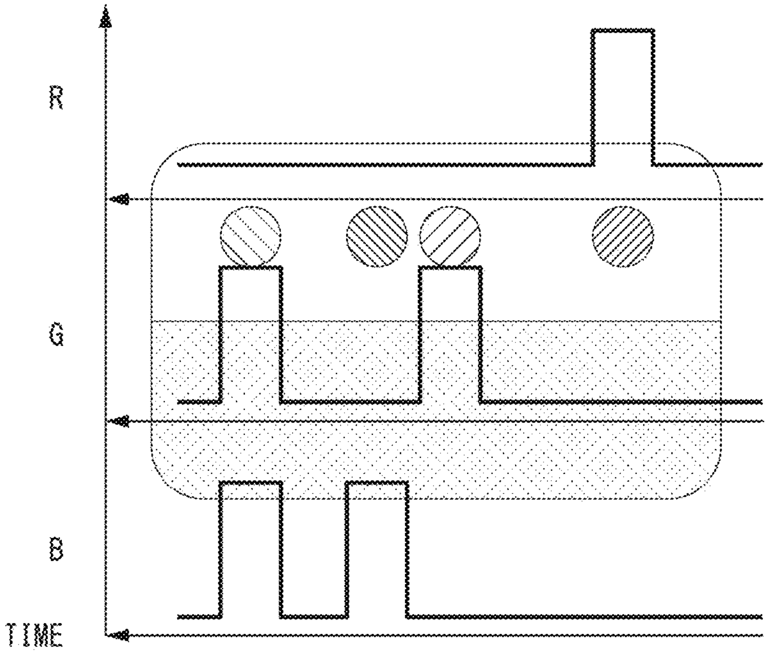
FIG. 20 is a diagram showing an example of results of measuring spatial barcode information and optical information according to Modified Example 2 of the first embodiment of the present invention.

In FIG. 20, a diagram showing an example of results of measuring spatial barcode information and optical information in the line detector 40*b* is shown. In FIG. 20, time-series changes in results of measuring colors of the beads Bb included in the compartment Pb for each color of red (R), green (G), and blue (B) fluorochromes are shown. In the example shown in FIG. 19, the bead Bb-1, the bead Bb-2, the bead Bb-3, and the bead Bb-4 are arranged in a line in that order in the movement direction (the flow velocity direction) of the compartment Pb. Here, the bead Bb-1 contains a red fluorochrome. The bead Bb-2 contains a green fluorochrome. The bead Bb-3 contains a blue fluorochrome. The bead Bb-4 contains green and blue fluorochromes and is yellow.

As indicated in the measurement results of the line detector 40*b*, the one-dimensional arrangement information of the beads Bb in the compartment Pb is converted into time-series information together with the color information. That is, spatial barcode information is processed as temporal barcode information together with optical information.

Although an example in which the beads Bb are arranged in a line in the flow velocity direction within the compartment Pb has been described in the present modified example, the arrangement is not limited thereto. The beads Bb may be arranged in two lines in the flow velocity direction within the compartment Pb. When the beads Bb are arranged in two lines in the flow velocity direction within the compartment Pb, the bead Bb included in the first line and the bead Bb included in the second line are arranged such that they do not overlap in a direction perpendicular to the flow velocity direction.

In the present modified example, spatial barcode information can be detected at a low error rate in a line scan process of measuring intensity levels according to fluorochrome concentrations of the beads Bb in the line detector 40*b*. Here, the beads Bb do not overlap each other in the movement direction (the flow velocity direction) of the compartment Pb and only a small amount of calculation is required for the line scan process. Therefore, in the present modified example, spatial barcode information can be accurately read with a small amount of calculation.

Next, a method of generating the compartment Pb will be described with reference to FIGS. 21 and 22.

In the present modified example, as an example, beads or particles are arranged in a line in the flow velocity direction within the compartment Pb using a method of concentrating beads or particles at nodes of an acoustic standing wave due to acoustic effects. In the following description, the method of concentrating beads or particles at nodes of an acoustic standing wave due to acoustic effects is referred to as acoustic focusing. For example, the methods described in Non-Patent Documents 2 and 3 are used for the acoustic focusing.

Figure 21:
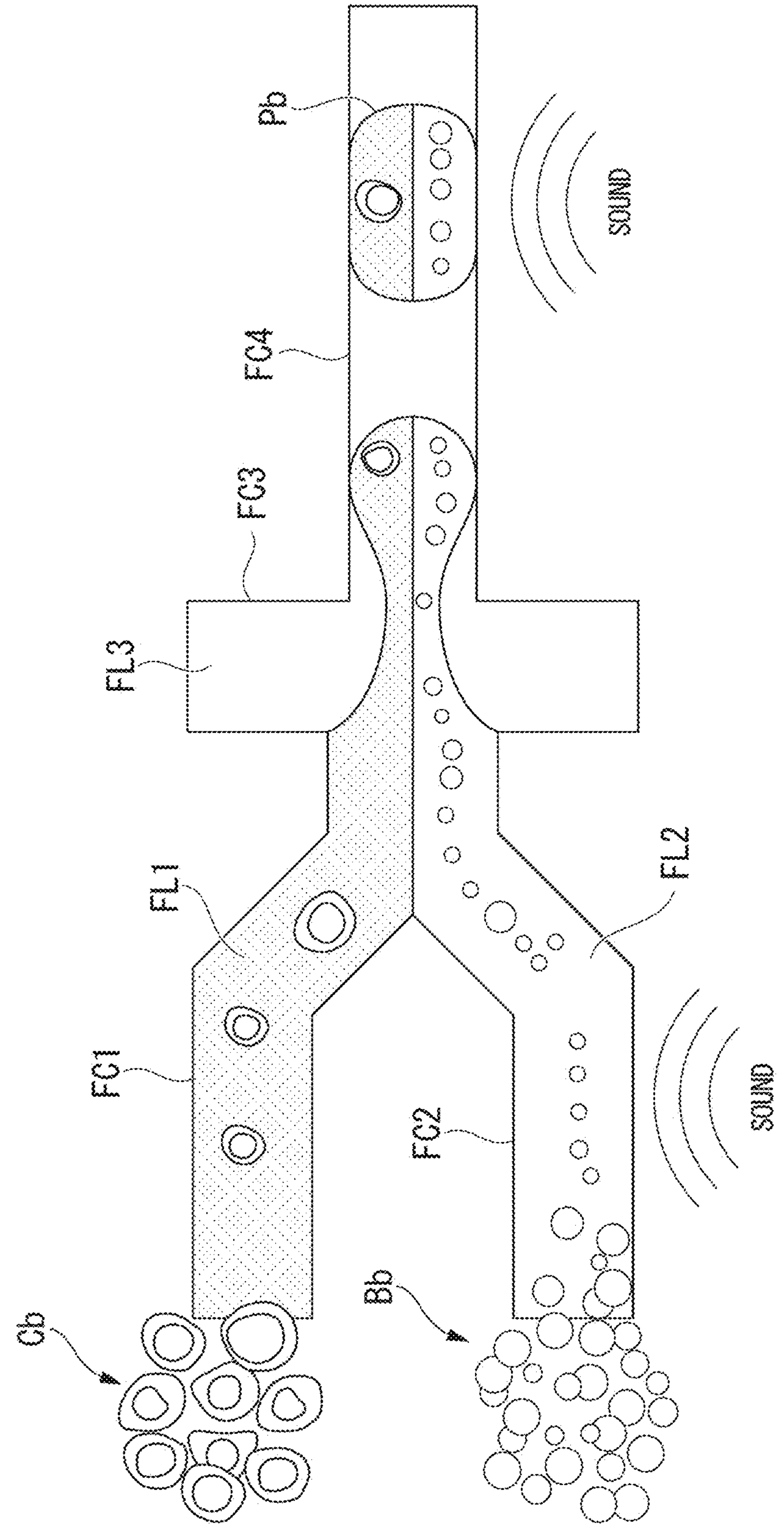
FIG. 21 is a diagram showing an example of a compartment generation method according to Modified Example 2 of the first embodiment of the present invention.

FIG. 21 is a diagram showing an example of a method of generating the compartment Pb according to the present modified example. A fluid FL1 including cells Cb flows along a flow path FC1. On the other hand, a fluid FL2 including beads Bb flows along a flow path FC2.

The beads Bb are irradiated with sound waves from an acoustic element in the flow path FC2 in a state in which the beads Bb are included in the fluid FL2. For example, ultrasonic waves are used as the sound waves emitted from the acoustic element, but the sound waves may be sound waves with a frequency lower than that of the ultrasonic waves. The beads Bb are aligned in a line in the flow velocity direction of the fluid FL2 due to the effect of acoustic focusing. The beads Bb are aligned in a line and separated from the walls of the flow path FC2.

The fluid FL1 and the fluid FL2 are allowed to merge with each other in the flow path FC4. In addition to the merged fluids FL1 and FL2, a fluid FL3 whose component is oil flows from the flow path FC3 to the flow path FC4. A compartment Pb, which is a droplet, is formed by the inflow of the fluid FL3 from the fluids FL1 and FL2 merging with each other. The formed compartment Pb is divided into two parts that are an upper part and a lower part in a direction perpendicular to the flow velocity direction of the flow path. The upper part is formed by including the cells Cb in the components of the fluid FL1 and the lower part is formed by including the beads Bb in the components of the fluid FL2.

When the compartment Pb, which is a droplet, is formed, the compartment Pb quickly begins to form a gel by reacting with the fluid FL3. During the gelation process of the compartment Pb, the beads Bb and the cells Cb are irradiated with ultrasonic waves from the acoustic element in the flow path FC4 in a state in which the beads Bb and the cells Cb are included in the compartments Pb. The beads Bb and the cells Cb are aligned in a line in the flow velocity direction of the flow path FC4 in the compartment Pb due to the effect of acoustic focusing. Here, the beads Bb are aligned in the upper part within the compartment Pb and the cell Cb is aligned in the lower part within the compartment Pb.

Here, the fluid FL1 and the fluid FL2 are, for example, different types of alginic acid gels. Also, examples of the beads Bb include collagen, agarose, and polyethylene glycol diacrylate (PEGDA), and the like. A material used for the beads Bb does not dissolve in the alginic acid gel used for the fluid FL.

Figure 22:
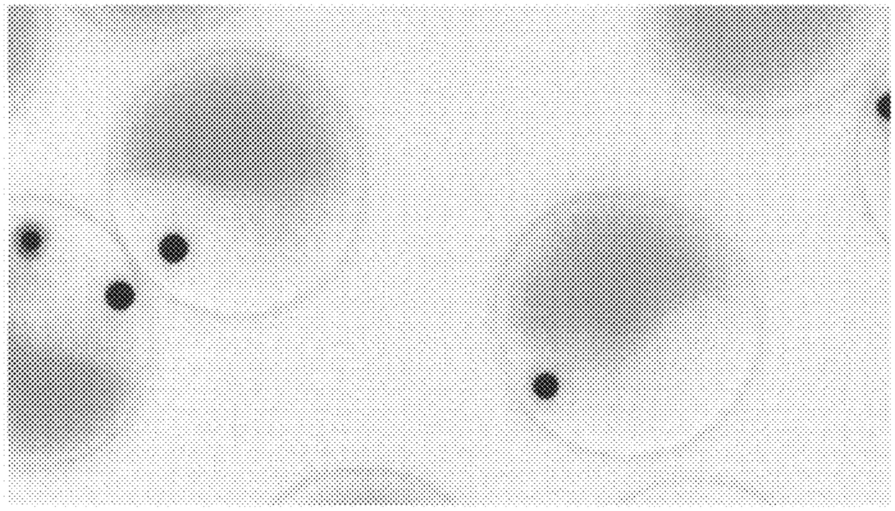
FIG. 22 is a diagram showing an example of a compartment according to Modified Example 2 of the first embodiment of the present invention.

FIG. 22 is a diagram showing an example of a compartment according to the present modified example. The compartment shown in FIG. 22 consists of two parts, each consisting of two types of gels. One of the two parts includes one or more fluorescent beads. As shown in FIG. 22, a compartment including the two parts can be generated and fluorescent beads can be arranged in one of the two parts. Although the other of the two parts of the compartment does not include a cell in the example shown in FIG. 22, the compartment is used in a state in which a cell is included in the other part when the cell flows through the flow cytometer.

Although an example in which the compartment Pb is a gel has been described in the present modified example, the present invention is not limited thereto. The compartment Pb may be a droplet. When the compartment Pb is a droplet, the arrangement of the beads Bb within the compartment Pb more easily changes as compared with a case where the compartment Pb is a gel. Thus, when the compartment Pb is a droplet, the measurement is performed by the line detector in a period before the arrangement of the bead Bb within the compartment Pb changes after the bead Bb is arranged within the compartment Pb.

Modified Example 3

In the present embodiment, an example in which the identifier is imaging information has been described. As a modified example, a case where the identifier is a type or a combination of types of fluorescent molecules constituting an identification substance will be described. In the following description, the identification substance of the present modified example is also referred to as a spectrum barcode. A compartment generation portion according to Modified Example 3 is referred to as a compartment generation portion 1*b*.

Figure 23:
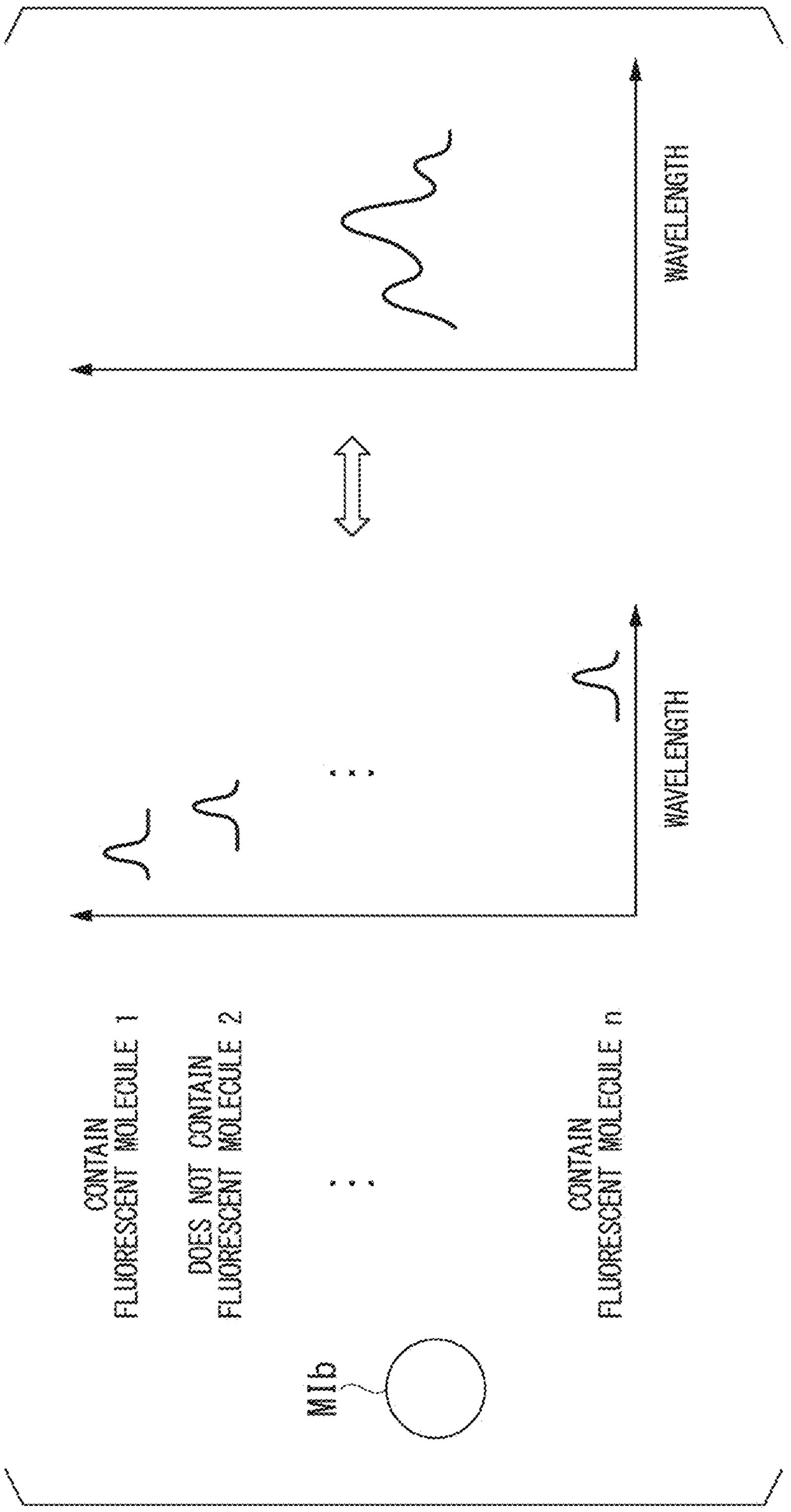
FIG. 23 is a diagram showing an example of a spectrum barcode according to Modified Example 3 of the first embodiment of the present invention.

FIG. 23 is a diagram showing an example of a spectrum barcode according to the present modified example.

In Modified Example 3, the identification substance MIb is a fluorescent substance including a plurality of types of fluorescent molecules. The plurality of types of fluorescent molecules each emit fluorescence having a specific wavelength. The identification substance MIb emits fluorescence having a wavelength spectrum according to a type, a concentration, or a combination of types of fluorescent molecules that are constituent components. Thus, the identification substance MIb can be identified by analyzing the wavelength spectrum of fluorescence emitted by the identification substance MIb.

Also, it is not necessary to identify a type, a concentration, or a combination of types of fluorescent molecules constituting the identification substance MIb such that the identification substance MIb is identified and the identification substance MIb may be identified using a wavelength spectrum. That is, the spectrum of the identification substance MIb may be used as the identifier Db. A type, a concentration, or a combination of types of fluorescent molecules constituting the identification substance MIb may be identified from the wavelength spectrum such that the identification substance MIb is identified and the identification substance MIb may be identified from the identified type, concentration, or combination of types of fluorescent molecules.

Thus, the identification substance MIb includes fluorescent molecules and the identifier Db is a spectrum of the identification substance MIb or the type, concentration, or combination of types of fluorescent molecules constituting the identification substance MIb.

Also, even if the identification substance MIb and the cell are not spatially separated within the compartment, the spectrum of the identification substance MIb can be measured without interfering with the cell information of the cell.

Figure 24:
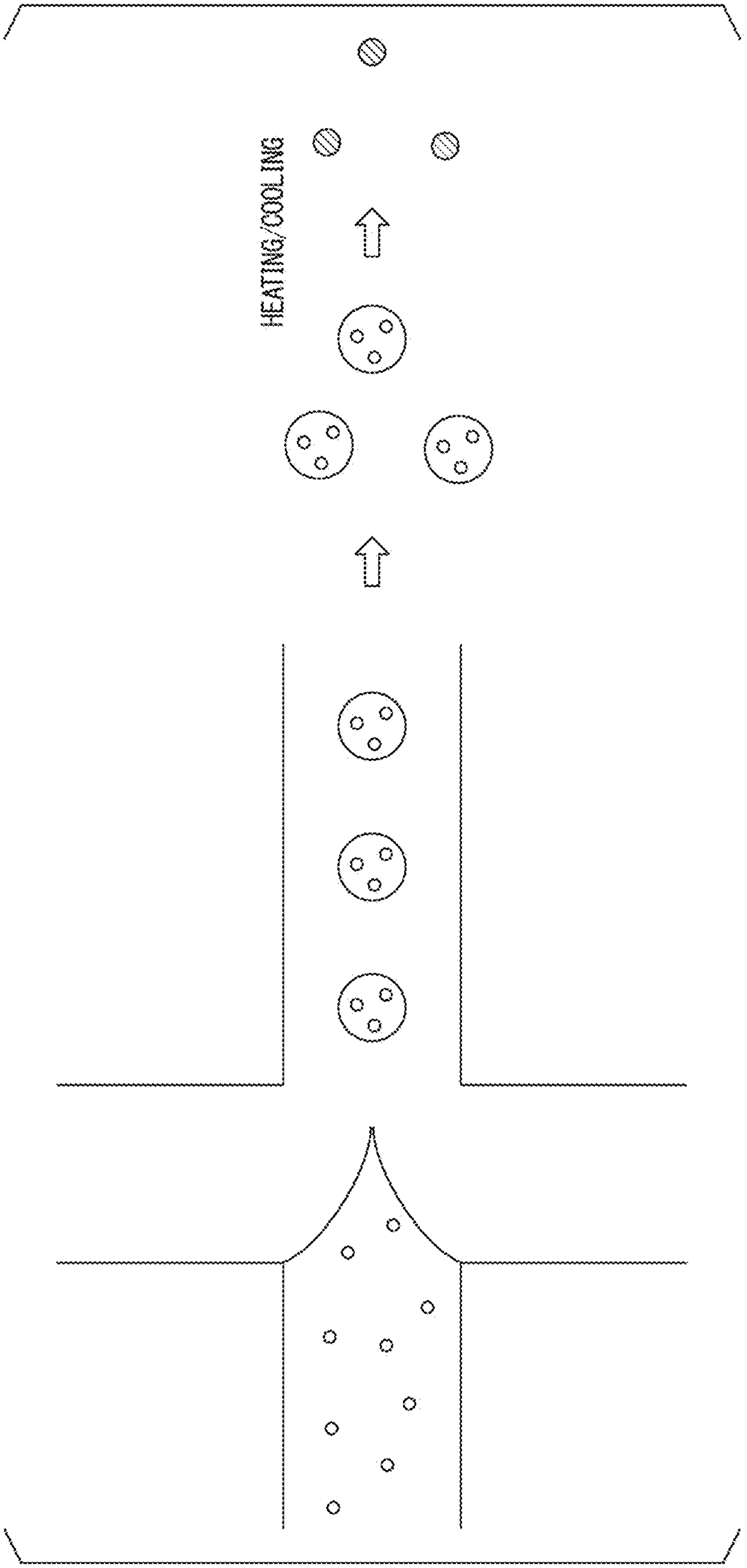
FIG. 24 is a diagram showing an example of a spectrum barcode generation method according to Modified Example 3 of the first embodiment of the present invention.

Here, a spectrum barcode generation method will be described with reference to FIG. 24. FIG. 24 is a diagram showing an example of the spectrum barcode generation method according to the present modified example. The compartment generation portion 1*b* forms a droplet from a liquid in which a plurality of types of fluorescent molecules are randomly mixed. The fluorescent molecules and droplets are, for example, agarose. The agarose of the fluorescent molecules and the agarose of the droplets have melting points different from each other. The compartment generation portion 1*b* melts only the agarose in the droplet due to heating and releases the fluorescent molecules included in the droplet outside of the droplet such that they are close to each other. The compartment generation portion 1*b* cools the released fluorescent molecules and a plurality of types of fluorescent molecules are allowed to aggregate to form a fluorescent substance.

The compartment generation portion 1*b* generates the compartment Pb by allowing fluids including the identification substance MIb, which is the formed fluorescent substance, and the cell C to merge with each other to form a droplet.

As described above, in the cell analysis device according to the present modified example, the identification substance MIb includes fluorescent molecules and the identifier Db is a spectrum of the identification substance MIb, a type of the fluorescent molecules constituting the identification substance MIb, a concentration of the fluorescent molecules constituting the identification substance MIb, or a combination of types of fluorescent molecules constituting the identification substance MIb.

According to this configuration, in the cell analysis device according to the present modified example, because the number of types of identification substances MIb can be increased in accordance with a type, a concentration, or a combination of types of fluorescent molecules, it is possible to increase the number of types of compartments capable of being identified in accordance with the type, concentration, or combination of types of fluorescent molecules.

Modified Example 4

In the present embodiment, an example in which a compartment includes an identification substance together with a cell and the cell is identified on the basis of an identifier of the identification substance has been described. As a modified example, a case where a cell is identified using an intensity distribution (spectrum) of fluorescence included in the cell for each wavelength will be described. Here, the fluorescence included in the cell may be derived from a molecular label or may be due to autofluorescence. In the following description, a cell that emits fluorescence is referred to as a fluorescent cell CF. Also, a fluorescence spectrum of the fluorescent cell CF is referred to as a fluorescence spectrum FS. Also, the cell information of the present modified example is referred to as cell information ICf.

Figure 25:
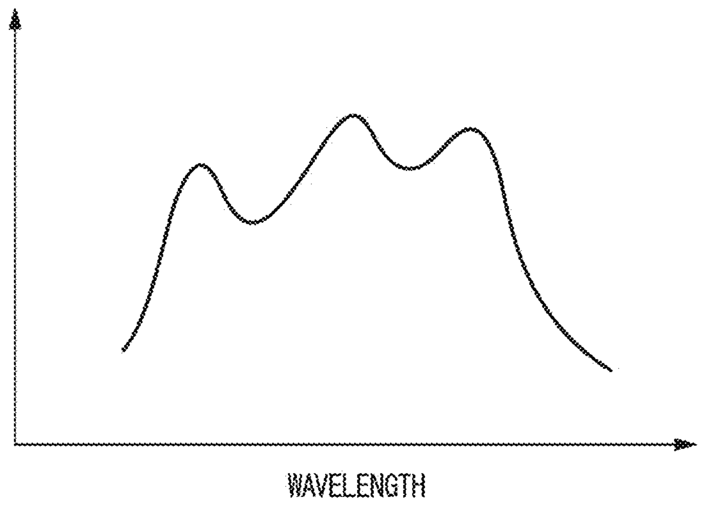
FIG. 25 is a diagram showing an example of a fluorescence spectrum according to Modified Example 4 of the first embodiment of the present invention.

FIG. 25 is a diagram showing an example of the fluorescence spectrum FS according to the present modified example. The fluorescence spectrum FS is generated, for example, by detecting the fluorescence of the fluorescent cell CF flowing along the flow path of the flow cytometry device 4 using a detector. This detector is, for example, a line PMT (a photomultiplier tube) in which a photomultiplier tube is arranged in a line shape. Here, the detector has a function of a spectrum analyzer and generates a fluorescence spectrum FS by analyzing the intensity of the detected fluorescence for each wavelength on the basis of spectral analysis.

The analysis device 3 associates the fluorescence spectrum FS with the cell information ICf. Here, in the present modified example, the cell information ICf is, for example, information indicating the fluorescent cell CF generated on the basis of the intensity spectrum of the fluorescence emitted by the fluorescent cell CF. The cell information ICf may be generated in advance by the analysis device 3 or may be generated by a device other than the analysis device 3 (for example, a spectrum analyzer) and supplied to the analysis device 3. In the present modified example, an example in which the analysis device 3 has the function of a spectrum analyzer and generates the cell information ICf will be described.

Here, a process in which the analysis device 3 generates the cell information ICf will be described. The analysis device 3 generates the cell information ICf by executing spectrum analysis and gating processes for fluorescence emitted due to autofluorescence when the fluorescent cell CF flowing along the flow path of the flow cytometry device 4 is irradiated with a laser.

When the cell information ICf is generated on the basis of spectral analysis, the analysis device 3 generates a fluorescence intensity distribution for a wavelength on the basis of an intensity of fluorescence emitted by the fluorescent cells CF through a spectroscopic process. The analysis device 3 decomposes the generated fluorescence intensity distribution into fluorescence intensity distributions emitted from specific fluorescent molecules included in the fluorescent cells CF through deconvolution. In this decomposition process, a fluorescence intensity distribution for a wavelength of fluorescence emitted from a specific fluorescent molecule and the number of specific fluorescent molecule included in the fluorescent cells CF are calculated. For example, the analysis device 3 calculates a set of the number of fluorescent molecules included in the fluorescent cells CF as the cell information ICf.

When the cell information ICf is generated on the basis of gating, the analysis device 3 generates distributions associated with an intensity of forward scatter (FSC) and an intensity of side scatter (SSC) with respect to a plurality of fluorescent cells CF for fluorescence emitted by the fluorescent cells CF flowing along the flow path of the flow cytometry device 4. The analysis device 3 extracts a distribution of specific cells among the plurality of fluorescent cells CF in a gate analysis process from the generated distributions. The analysis device 3 calculates a set of the FSC intensity and the SSC intensity based on the extracted distribution as the cell information ICf for a specific cell among the plurality of fluorescent cells CF. Here, information about the shape and size of a cell can be obtained from the FSC and information about the granularity and complexity of a cell can be obtained from the SSC. In other words, the analysis device 3 uses the cell information ICf that is a set of the FSC intensity and the SSC intensity based on the extracted distribution as information indicating the shape, size, granularity, complexity, and the like of the cell that is the fluorescent cell CF.

Also, the analysis device 3 may include both a set of the number of fluorescent molecules included in the above-described fluorescent cell CF and the set of the FSC intensity and the SSC intensity in the cell information ICf.

For example, the analysis device 3 associates the fluorescence spectrum FS with the cell information ICf on the basis of pattern matching or machine learning.

When pattern matching is used for association, the analysis device 3 associates the measured fluorescence spectrum FS with the measured cell information ICf with respect to each of the plurality of fluorescent cells CF. As a result of this association process, the analysis device 3 generates a plurality of patterns of fluorescence spectra FS associated with a plurality of pieces of cell information ICf. The analysis device 3 outputs the plurality of patterns of fluorescence spectra FS, which have been generated, as templates to the cell analysis device 6.

When machine learning is used for association, the analysis device 3 executes supervised machine learning using data obtained by pairing the measured fluorescence spectrum FS and the measured cell information ICf with respect to a plurality of fluorescent cells CF as training data. The analysis device 3 generates a model for calculating the cell information ICf when the fluorescence spectrum FS is input as a result of this supervised machine learning. The analysis device 3 outputs the generated model to the cell analysis device 6.

In the determination process, the cell analysis device 6 determines the fluorescent cell CF from the fluorescence spectrum FS of the fluorescent cell CF measured by the flow cytometry device 4 on the basis of pattern matching or machine learning.

The cell analysis device 6 acquires cell information ICf about the determination target input from the determination target input portion 5. The information representing the cell information ICf is designated by, for example, the set of the number of fluorescent molecules for the fluorescent cell CF of the determination target and the shape, size, granularity, and complexity of the cell as described above.

When pattern matching is used to determine the fluorescent cells CF, the cell analysis device 6 selects a pattern of the fluorescence spectrum FS corresponding to the cell information ICf for the determination target from among the plurality of patterns included in the template generated by the analysis device 3. The cell analysis device 6 determines whether or not the fluorescence spectrum FS measured for the fluorescent cell CF flowing along the flow path of the flow cytometry device 4 matches a preselected pattern. When it is determined that the measured fluorescence spectrum FS matches the preselected pattern, the cell analysis device 6 determines the fluorescent cell CF flowing along the flow path as the determination target.

When machine learning is used to determine the fluorescent cell CF, the cell analysis device 6 calculates the cell information ICf for the fluorescence spectrum FS measured for the fluorescent cells CF flowing along the flow path of the flow cytometry device 4 on the basis of a model generated by the analysis device 3. The cell analysis device 6 determines whether or not the cell information ICf calculated using the model matches the cell information ICf for the determination target. Also, the cell information ICf for the determination target may be designated by a range of the number of fluorescent molecules or a range of the size of the fluorescent cell CF. The case where the calculated cell information ICf matches the cell information ICf for the determination target also includes the case where the number of fluorescent molecules or the size of the fluorescent cell CF indicated in the cell information ICf is included in a range indicated in the cell information ICf for the determination target. When the calculated cell information ICf matches the cell information ICf for the determination target, the cell analysis device 6 determines the fluorescent cells CF flowing along the flow path as the determination target.

Also, the cell identification method of the present modified example may be used in combination with the cell identification method of the above-described embodiment or the above-described modified example. For example, a fluorescent cell CF is included in the compartment together with an identification substance. After the fluorescent cell CF is determined using the identification substance, the cell analysis device 6 may further determine the fluorescent cell CF using the fluorescence spectrum FS of the fluorescent cell CF. The cell analysis device 6 determines whether or not the fluorescent cell CF is a determination target, for example, in one or both of the determination based on the identification substance and the determination based on the fluorescence spectrum FS. Thereby, the determination based on the fluorescence spectrum FS of the present modified example can be used as an aid to the determination based on the identification substance of the above-described embodiment or modified example.

Also, the cell identification method of the present modified example can also be applied to the identification of bacteria in addition to cells. That is, the cell identification method of the present modified example may be used to identify bacteria using the intensity distribution (the spectrum) for each wavelength of fluorescence included in bacteria.

Second Embodiment

A second embodiment of the present invention will be described in detail below with reference to the drawings.

In the above-described first embodiment, the case where a bead, which is an identification substance, has imaging information as an identifier has been described. In the present embodiment, the case where a bead, which is an identification substance, has nucleic acid sequence information of a cell in addition to imaging information will be described.

A cell sorting system according to the present embodiment is referred to as a cell sorting system CSc.

Figure 26:
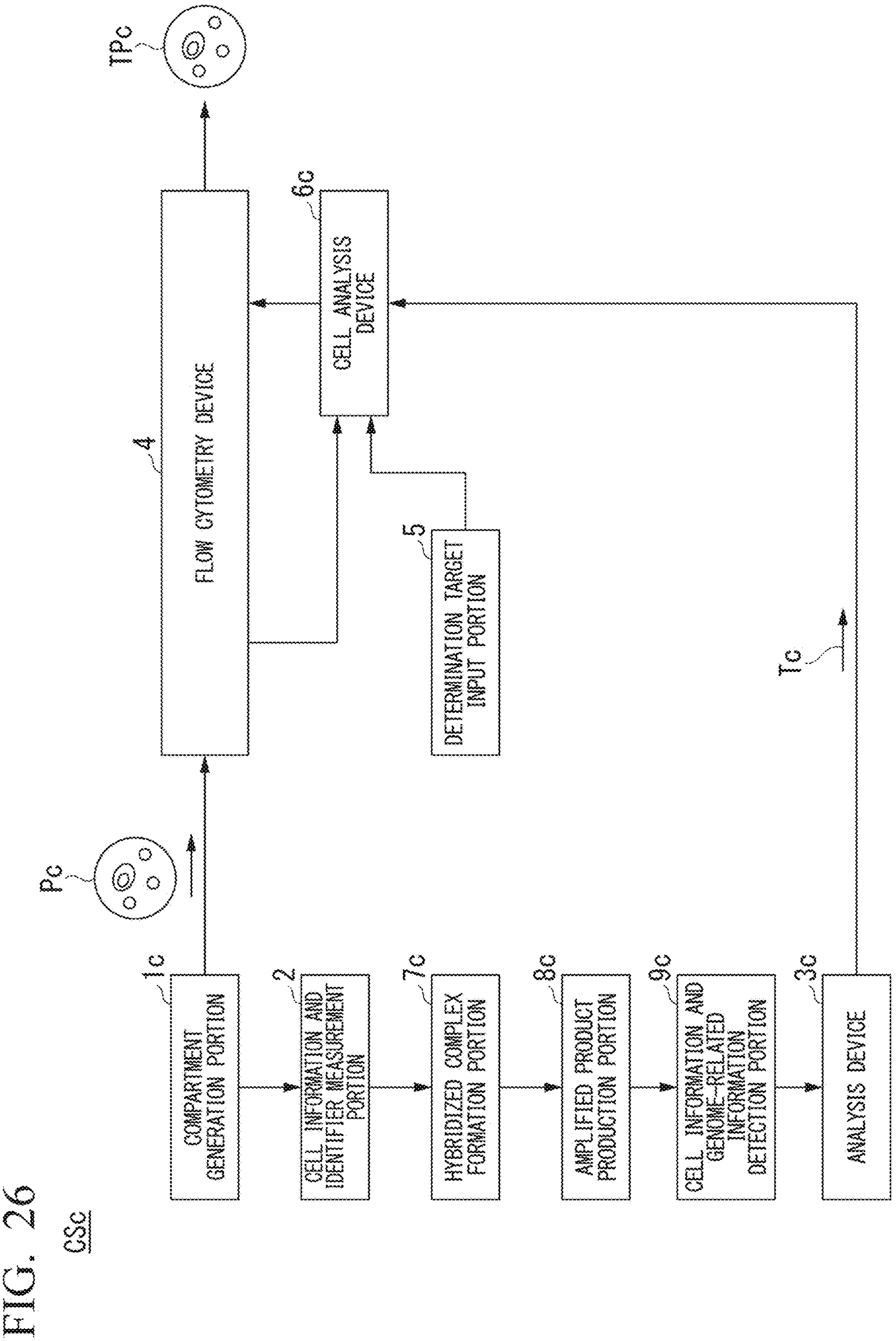
FIG. 26 is a diagram showing an example of a cell sorting system according to a second embodiment of the present invention.

FIG. 26 is a diagram showing an example of the cell sorting system CSc according to the present embodiment. The cell sorting system CSc includes a compartment generation portion 1*c*, a cell information and identifier measurement portion 2, an analysis device 3*c*, a flow cytometry device 4, a determination target input portion 5, a cell analysis device 6*c*, a hybridized complex formation portion 7*c*, an amplified product production portion 8*c*, and a cell information and genome-related information detection portion 9*c*. When the cell sorting system CSc (FIG. 26) according to the present embodiment is compared with the cell sorting system CS (FIG. 1) according to the first embodiment, the compartment generation portion 1*c*, the analysis device 3*c*, the cell analysis device 6*c*, the hybridized complex formation portion 7*c*, the amplified product production portion 8*c*, and the cell information and genome-related information detection portion 9*c* are different. Here, the functions of the other components (the cell information and identifier measurement portion 2, the flow cytometry device 4, and the determination target input portion 5) are the same as those in the first embodiment. Description of the functions that are the same as those in the first embodiment will be omitted and description of the second embodiment will focus on parts different from those in the first embodiment.

A compartment generation portion 1*c* generates a compartment Pc. In the present embodiment, the compartment Pc includes an identification substance MIc. For example, a bead B has imaging information IB that is information capable of being identified through imaging. The identification substance MIc is configured to include a bead Bc and a nucleic acid linked to the bead Be such that linkage is cleavable. This bead Bc has imaging information IB, which is information capable of being identified through imaging, as in the first embodiment. As will be described below, the beads Bc include two types of first and second beads B1 and B2.

Figure 27:
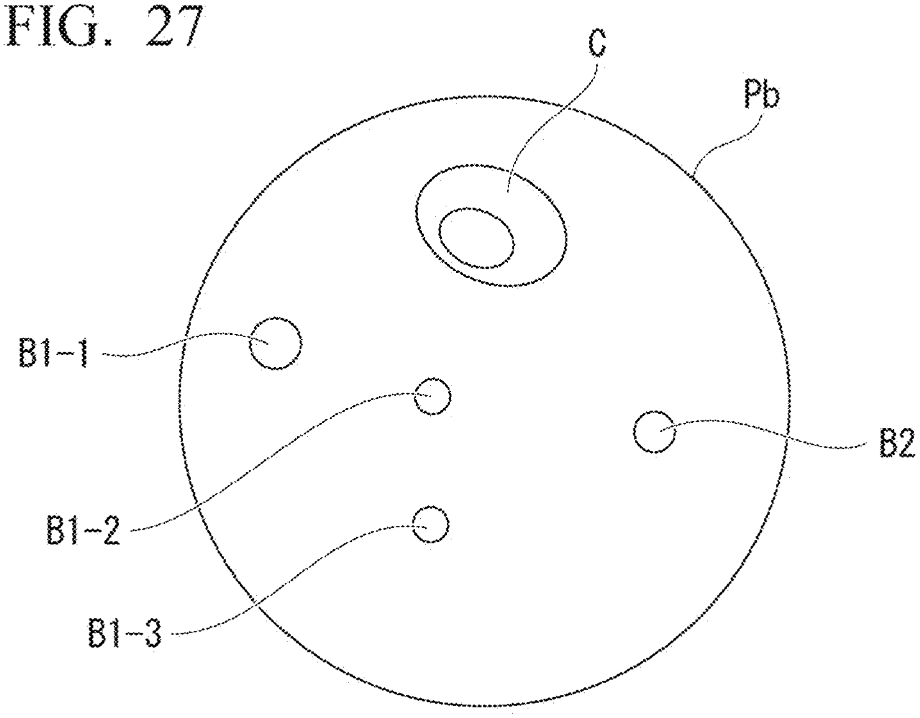
FIG. 27 is a diagram showing an example of a compartment according to the second embodiment of the present invention.

Here, the compartment Pc will be described with reference to FIG. 27. FIG. 27 is a diagram showing an example of the compartment Pc according to the present embodiment. The compartment Pc includes one cell C per droplet, a first bead B1, and a second bead B2. In the example shown in FIG. 27, the compartment Pc includes a plurality of first beads B1 that are a first bead B1-1, a first bead B1-2, and a first bead B1-3.

The cell C has genome-related information IG. The genome-related information IG is nucleic acid sequence information derived from a genome-related nucleic acid corresponding to a cell genome or its expression product. The genome-related nucleic acid is a nucleic acid probe specific to a molecule such as a genomic deoxyribonucleic acid (DNA) of a cell C, a ribonucleic acid (RNA) such as a messenger RNA (mRNA) derived from the cell genome, its complementary DNA (cDNA), or a protein expressed in the cell C. A nucleic acid probe preferably includes a mutually distinguishable nucleic acid (a barcode nucleic acid to be described below) linked to a molecule that is specifically linked to a molecule such as a target protein such that linkage is cleavable.

Also, when the nucleic acid is genomic DNA, this DNA may be a cleaved fragment using a restriction enzyme or the like or may have a DNA tag introduced therein.

It is only necessary for the number of second beads B2 per compartment to be one or more. The number of second beads B2 per compartment is preferably one such that genome-related information IG derived from the same cell C is identified.

Here, the first bead B1 and the second bead B2 will be described with reference to FIGS. 28 to 31.

Figure 28:
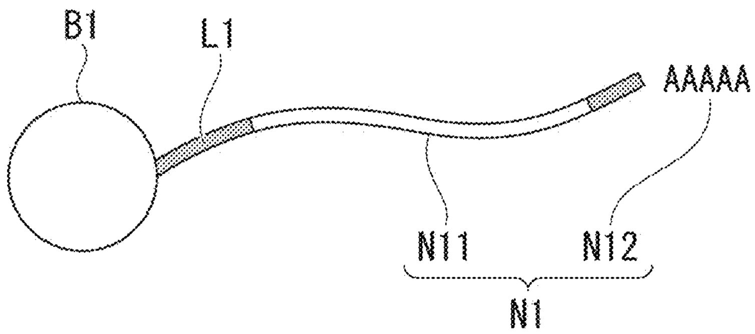
FIG. 28 is a diagram showing an example of first beads according to the second embodiment of the present invention.

FIG. 28 is a diagram showing an example of the first bead B1 according to the present embodiment. A first barcode nucleic acid N1 is linked to the first bead B1 such that linkage is cleavable.

As described above, the first bead B1 has imaging information IB that is information capable of being identified through imaging. In the present embodiment, a bead may be any type of particle having a shape as long as it is a particle to which a barcode nucleic acid can be linked. The material of the first bead B1 is similar to the material of the bead B of the first embodiment.

The first barcode nucleic acid N1 is included in the types of barcode nucleic acids. The barcode nucleic acids are described here.

The barcode nucleic acid is a nucleic acid containing a barcode region. This barcode region enables identification of the genome-related information IG of the cell C and the imaging information IB included in the bead B. The barcode region is a region of a random base sequence including A (adenine), G (guanine), C (cytosine), and T (thymine).

There are two types of barcode regions that are a common barcode region and a unique barcode region.

The common barcode region is a common barcode region in the same identification target.

When the identification target is the genome-related information IG of the cell C, the common barcode region differs according to each cell. That is, the common barcode region is a common barcode region for one cell C. By using the common barcode region as a label, genome-related information IG derived from the same cell C can be identified.

Also, when the identification target is the imaging information IB of the beads B, it is a barcode region common to the beads B having the same imaging information IB. By using the common barcode region as a label, the imaging information IB of the beads B having the same imaging information IB can be identified.

A nucleic acid probe specific to a molecule such as a protein expressed in the cell C includes a molecule specifically combined with a molecule (a binding molecule). The common barcode region also includes a different barcode region for each binding molecule in the nucleic acid probe. That is, a barcode region, which is common between identical binding molecules, is included in the common barcode region.

A first barcode nucleic acid N1 is a barcode nucleic acid including a barcode region corresponding to the imaging information IB of the first bead B1. That is, the first barcode nucleic acid N1 is a type of nucleic acid corresponding to the imaging information IB. The first barcode nucleic acid N1 includes a first common barcode region N11 and a first hybridizing region N12.

A type of the first barcode nucleic acid N1 is not particularly limited as long as it includes a barcode region.

The first barcode nucleic acid N1 is, for example, RNA, DNA, or a combination thereof.

Also, a unique barcode region makes it possible to identify each barcode nucleic acid using a different barcode region for each barcode nucleic acid as a label. A bead B linked to each barcode nucleic acid and a genome-related nucleic acid hybridized with each barcode nucleic acid can be identified using the unique barcode region.

Although a length of the barcode region is not particularly limited, it is preferably a sequence with a length of 10 to 40 bases. For example, if the barcode region has a length of 12 bases, $4^{12}$ types of different barcode nucleic acids can be amplified at once and $4^{12}$ types of beads B can be generated.

The first common barcode region N11 is a barcode region corresponding to the imaging information IB of the first bead B1. The first barcode nucleic acid N1 corresponds one-to-one to the imaging information IB of the first bead B1 to which the first barcode nucleic acid N1 is linked using sequence information of the first common barcode region N11.

The first hybridizing region N12 is included in the types of hybridizing regions. Here, the hybridizing region will be described.

First, in the present embodiment, hybridization is a process in which the hybridizing region of the barcode nucleic acid forms a double-stranded complex with a genome-related nucleic acid corresponding to the cellular genome or its expression product or another barcode nucleic acid under a stringent condition. Here, the stringent condition is a condition under which a so-called specific complex is formed and a non-specific complex is not formed.

A hybridizing region is a region that can be combined (hybridized) with a genome-related nucleic acid corresponding to the cellular genome or its expression product or another barcode nucleic acid.

The first hybridizing region N12 is a region that can be hybridized with the second barcode nucleic acid N2 linked to the second bead B2.

A cleavable linker L1 links the first bead B1 to the first barcode nucleic acid N1 such that linkage is cleavable. The cleavable linker L1 is, for example, a chemically cleavable linker, a linker photocleavable with UV or the like, a thermally cleavable linker, an enzymatically cleavable linker, or the like. Photocleavable linkers include, for example, photocleavable (PC)-biotin, iSpPC, and the like and chemically cleavable linkers include, for example, disulfide bonds and the like.

By using the cleavable linker L1, the linked first barcode nucleic acid N1 can be cleaved from the first bead B1 and separated or released.

In addition to the first common barcode region N11, the first barcode nucleic acid N1 may further include a unique barcode region and a primer region that can be distinguished from each other.

The first bead B1 may have an acrylamide moiety via the cleavable linker L1.

Figures 29, 30:
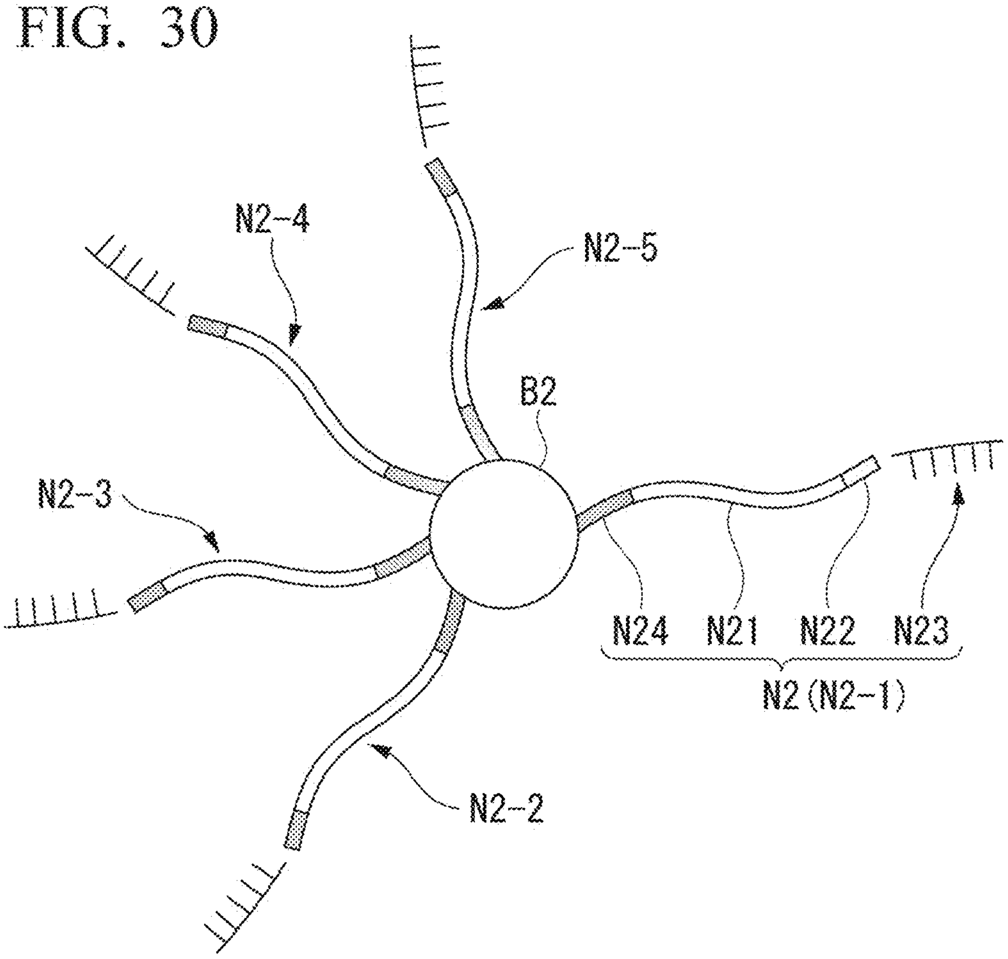
FIG. 29 is a diagram showing an example of information associated with the first beads according to the second embodiment of the present invention.
FIG. 30 is a diagram showing an example of second beads according to the second embodiment of the present invention.

FIG. 29 is a diagram showing an example of information associated with the first bead B1 according to the present embodiment. In FIG. 29, information associated with the first beads B1 is shown for each of the first beads B1 with the bead numbers #1, #2, and #3 as the labels of types of first beads B1.

As described above, the first bead B1 has imaging information IB. In FIG. 29, the intensity level according to the fluorochrome concentration for each of the three colors (red, green, and blue) of the fluorochrome is shown as an example of the imaging information IB.

Also, as described above, the first barcode nucleic acid N1 is linked to the first bead B1 such that linkage is cleavable and the first common barcode region N11 of the first barcode nucleic acid N1 corresponds to the imaging information IB of the first bead B1. In FIG. 29, a first barcode sequence, which is a base sequence of the first common barcode region N11 is shown.

For example, in the first bead B1 of bead number #1, the base sequence of "ATGCATGC . . . " in the first common barcode region N11 is associated with imaging information IB in which red, green, and blue fluorochrome concentrations are "3," "3," and "3."

Next, the second bead B2 will be described with reference to FIG. 30. FIG. 30 is a diagram showing an example of the second beads B2 according to the present embodiment. A second barcode nucleic acid N2 is linked to the second bead B2 such that linkage is cleavable. In the example shown in FIG. 30, five second barcode nucleic acids N2, which are second barcode nucleic acids N2-1 to N2-5, are linked to the second bead B2 such that linkage is cleavable.

The second bead B2 is preferably linked to 1000 to 100000 second barcode nucleic acids N2 such that it can hybridize with a large number of genome-related nucleic acids.

The material of the second bead B2 is, for example, similar to that of the first bead B1. Also, the material of the second bead B2 may be different from the material of the first bead B1. The material of the second bead B2 is preferably a hydrogel or resin. More preferably, the material of the second bead B2 is acrylamide, polystyrene, a hydrophilic vinyl polymer, a hydrophilic vinyl polymer with which PEG or its derivative is combined, or the like.

The second barcode nucleic acid N2 includes a second common barcode region N21, a second unique barcode region N22, a second hybridizing region N23, and a PCR primer region N24.

The second barcode nucleic acid N2 includes the PCR primer region N24, the second common barcode region N21, the second unique barcode region N22, and the second hybridizing region N23 in order from the second bead B2 side.

In FIG. 30, the above regions are shown with respect to the second barcode nucleic acid N2-1 as an example of the second barcode nucleic acid N2.

The type of the second barcode nucleic acid N2 is not particularly limited as long as it contains a barcode region. The second barcode nucleic acid N2 is, for example, RNA, DNA or a combination thereof. The second barcode nucleic acid N2 can be directly or indirectly linked to the second bead B2.

The second common barcode region N21 serves as an index for identifying the cell C included in the compartment P together with the second barcode nucleic acid N2. The second common barcode region N21 has a base sequence common between two or more second barcode nucleic acids N2 linked to the second beads B2. The second barcode nucleic acid N2 corresponds one-to-one to the cell C included in the compartment P together with the second bead B2 to which the second barcode nucleic acid N2 is linked using the sequence information of the second common barcode region N21.

The second unique barcode region N22 is a unique barcode region unique to each second barcode nucleic acid N2. In the present embodiment, the second unique barcode region N22 serves as an index for identifying a genome-related nucleic acid. This genome-related nucleic acid is a genome-related nucleic acid derived from the cell C included in the compartment P together with the second bead B2 to which the second barcode nucleic acid N2 is linked. The second barcode nucleic acid N2 corresponds one-to-one to the genome-related nucleic acid that hybridizes with the second hybridizing region N23 using the sequence information of the second unique barcode region N22.

The second hybridizing region N23 can hybridize with each of the genome-related nucleic acid and the first barcode nucleic acid N1. The second hybridizing region N23 preferably contains poly-thymine or a nucleic acid complementary to the genome-related nucleic acid.

For example, when the genome-related nucleic acid is mRNA, the second hybridizing region N23 in the second barcode nucleic acid N2 is preferably poly-thymine composed of T (thymine). A length of poly-thymine is preferably a length in which it can be annealed with the polyadenine (A) tail of mRNA. In this case, the first hybridizing region N12 is preferably a sequence complementary to that of poly-thymine, for example, polyadenine.

When the genome-related nucleic acid is DNA such as genomic DNA, the second hybridizing region N23 preferably contains a sequence complementary to a specific sequence of this DNA or a sequence of a DNA tag introduced into this DNA. In this case, the first hybridizing region N12 of the first barcode nucleic acid N1 preferably has a sequence complementary to that of the second hybridizing region N23.

When the nucleic acid probe specific to a molecule such as a protein expressed in the cell C contains a barcode nucleic acid and this barcode nucleic acid contains a hybridizing region, the second hybridizing region N23 preferably contains a sequence complementary to that of this hybridizing region. In this case, the first hybridizing region N12 of the first barcode nucleic acid N1 preferably has a sequence complementary to that of the second hybridizing region N23.

As described above, the second bead B2 is linked to a plurality of second barcode nucleic acids N2, which are genome-related nucleic acids corresponding to the genome of the cell C or expression products thereof, or nucleic acids capable of hybridizing with the first barcode nucleic acid N1.

FIG. 31 is a diagram showing an example of information associated with the second bead B2 according to the present embodiment. In FIG. 31, information associated with the second bead B2 for each of the second beads B2 with the bead numbers #1, #2, and #3 as labels of types of second beads B2 is shown.

As described above, the second bead B2 is linked to the second barcode nucleic acid N2 such that linkage is cleavable and the second common barcode region N21 of this second barcode nucleic acid N2 corresponds to the cell C included in the compartment P together with the second bead B2. Also, the second unique barcode region N22 of this second barcode nucleic acid N2 corresponds to the genome-related nucleic acid derived from the cell C included in the compartment P together with the second bead B2.

For example, the second bead B2 with bead number #1 is associated with "cell A" and "XXXXXXX" that is the genome of the genome-related nucleic acid of this "cell A."

Description of the cell sorting system CSc will be continued with reference to FIG. 26 again.

The cell analysis device 6*c* determines the determination target compartment TPc on the basis of the table Tc generated by the analysis device 3*c* and the identifier D detected by the flow cytometry device 4.

The hybridized complex formation portion 7*e* forms a hybridized complex by allowing the genome-related nucleic acid of the cell C included in the compartment Pc and the first barcode nucleic acid N1 linked to the first bead B1 such that linkage is cleavable to hybridize with the second barcode nucleic acid N2 combined with the second bead B2 such that linkage is cleavable.

The hybridized complex formation portion 7*c* includes a cleaving device for the cleavable linker L1 linked to the first barcode nucleic acid N1. This cleaving device may be selected in accordance with a type of cleavable linker L1. For example, if the cleavable linker L1 is iSpPC, the cleaving device is a UV irradiation device.

The hybridized complex formation portion 7*c* includes a reagent or a device for forming a hybridized complex. The reagent for forming the hybridized complex is, for example, a reagent normally used for hybridization of nucleic acids. An example of a device for forming a hybridized complex is a water bath.

The amplified product production portion 8*c* produces an amplified product derived from the hybridized complex formed by the hybridized complex formation portion 7*c*. The amplified product production portion 8*c* is, for example, a polymerase chain reaction (PCR) device.

When the genome-related nucleic acid NG is RNA, the amplified product production portion 8*c* produces an amplified product using reverse transcription and PCR as an example. When the genome-related nucleic acid NG is DNA, the amplified product production portion 8*c* produces an amplified product using extension PCR as an example. The amplified product production portion 8*c* uses a reagent used in normal reverse transcription or PCR reactions to produce an amplified product.

The cell information and genome-related information detection portion 9*c* detects the cell information IC and the genome-related information IG in association on the basis of the amplified product produced by the amplified product production portion 8*c*. That is, the cell information and genome-related information detection portion 9*c* integrally detects the cell information IC and the genome-related information IG. The cell information and genome-related information detection portion 9*c* includes, for example, a sequencer or a computer.

The cell information and genome-related information detection portion 9*c* detects the genome-related information IG by deciding on the base sequence information of the genome-related nucleic acid NG using a sequencer. The cell information and genome-related information detection portion 9*c* associates the cell information IC and the genome-related information IG with a computer.

The analysis device 3*c* generates a table Tc on the basis of the imaging information IB measured by the cell information and identifier measurement portion 2 and the cell information IC and the genome-related information IG detected by the cell information and genome-related information detection portion 9*c*. The table Tc is information of a table showing a corresponding relationship between the cell information IC and the identification substance MI for each compartment P. The analysis device 3*c* outputs the generated table Tc to the cell analysis device 6*c*.

Figure 32:
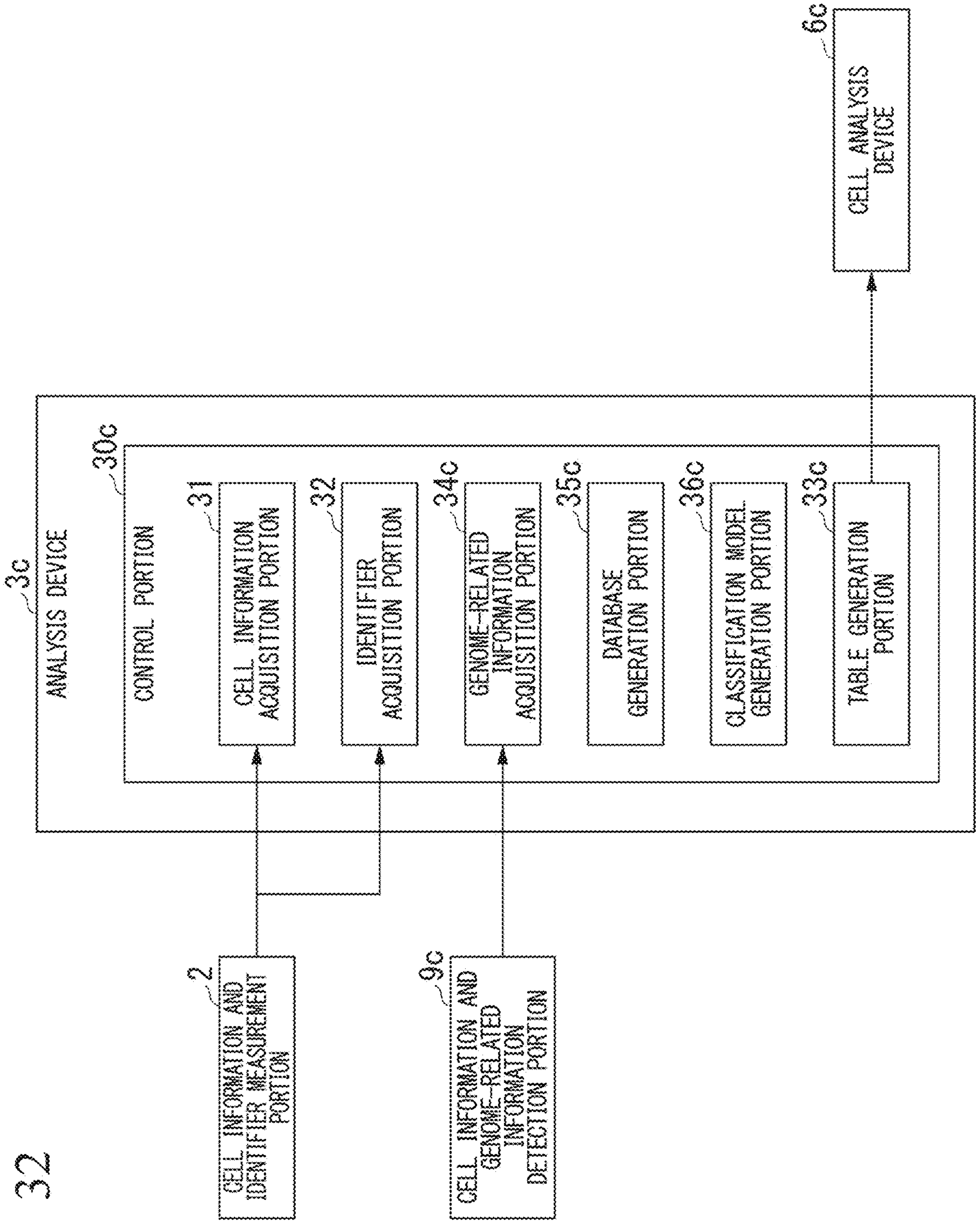
FIG. 32 is a diagram showing an example of a configuration of an analysis device according to the second embodiment of the present invention.

Here, a configuration of the analysis device 3*c* will be described with reference to FIG. 32. FIG. 32 is a diagram showing an example of the configuration of the analysis device 3*c* according to the present embodiment. The analysis device 3*c* includes a control portion 30*c*. The control portion 30*c* includes a cell information acquisition portion 31, an identifier acquisition portion 32, a table generation portion 33*c*, a genome-related information acquisition portion 34*c*, a database generation portion 35*c*, and a classification model generation portion 36*c*. When the analysis device 3*c* (FIG. 32) according to the present embodiment is compared with the analysis device 3 (FIG. 9) according to the first embodiment, the table generation portion 33*c*, the genome-related information acquisition portion 34*c*, the database generation portion 35*c*, and the classification model generation portion 36*c* are different. Here, the functions of other components (the cell information acquisition portion 31 and the identifier acquisition portion 32) are the same as those of the first embodiment. Description of the functions that are the same as those in the first embodiment will be omitted and description of the second embodiment will focus on parts different from those in the first embodiment.

The genome-related information acquisition portion 34*c* acquires the genome-related information IG associated with the cell information IC output by the cell information and genome-related information detection portion 9*c*.

The database generation portion 35*c* generates a database DB on the basis of the cell information IC acquired by the cell information acquisition portion 31 and the genome-related information IG acquired by the genome-related information acquisition portion 34*c*. The database DB is tabular data in which the cell information IC and the genome-related information IG are associated.

The classification model generation portion 36*c* generates a classification model MC on the basis of the database DB generated by the database generation portion 35*c*. The classification model MC is, for example, a model in which a relationship between cell information IC and cell classification results obtained by classifying cells C into a plurality of classes has been learned. As an example, the cell classification results are obtained by classifying the cells C into the plurality of classes on the basis of the genome-related information IG.

Here, the classification model generation portion 36*c* generates a classification model MC on the basis of machine learning. The classification model generation portion 36*c* executes machine learning using a set of the cell information IC and a class of the cell C indicated in the cell classification result as training data and generates the classification model MC. As an example, the classification model MC is a neural network. In this case, the classification model generation portion 36*c* generates the classification model MC on the basis of learning based on a neural network. The classification model generation portion 36*c* uses, for example, deep learning as learning based on a neural network. In the classification model MC, the class of the cell C for which the cell information IC is input is output.

Although an example in which the classification model generation portion 36*c* classifies the cells C into a plurality of classes by classifying the genome-related information IG into a plurality of classes has been described in the present embodiment, the present invention is not limited thereto. The classification model generation portion 36*c* may classify the cells C into a plurality of classes by classifying the cell information IC into a plurality of classes instead of the genome-related information IG.

When the cell information IC is classified into the plurality of classes, the classification model generation portion 36*c* executes machine learning using a set of the genome-related information IG and the class of the cell C indicated in the cell classification results as training data and generates a classification model MC.

The table generation portion 33*c* generates a table Tc on the basis of the classification model MC generated by the classification model generation portion 36*c* and the imaging information IB acquired by the determination target identifier extraction portion 62. The table generation portion 33*c* outputs the generated table Tc to the cell analysis device 6*c*.

Here, the table Tc generated by the table generation portion 33*c* will be described with reference to FIG. 33. FIG. 33 is a diagram showing an example of the table Tc according to the present embodiment. The table Tc is tabular data in which the class of the cell C, the cell information IC, the genome-related information IG, and the imaging information IB are associated with each compartment Pc. In FIG. 33, the classes of cells C are classified according to whether or not they respond to a certain chemical. Also, in FIG. 33, a cell image of the cell C is shown as the cell information IC.

The table Tc is generated on the basis of the classification model MC. When the table T in which the cell information IC and the imaging information IB are associated with each compartment Pc is given, the table generation portion 33*c* classifies the cell information IC included in the table T as the class of the cell C on the basis of the classification model MC. The table generation portion 33*c* generates the table Tc by associating the data included in the table T with the class of the cell C on the basis of the classification result.

Also, the table Tc may include the genome-related information IG in addition to the cell information IC.

Also, data of the cell information IC or genome-related information IG included in the table Tc is data separate from data of the cell information IC or the genome-related information IG included in the database DB used to generate the classification model MC. When the genome-related information IG is measured, the cell is destroyed and the cell does not become a sorting target.

In the table Tc shown in FIG. 33, as an example, the cell information IC or the genome-related information IG is classified on the basis of a feature of whether or not the cell responds to a certain chemical.

Also, when the classification model MC is generated in machine learning using the set of the genome-related information IG and the class of the cell C indicated in the cell classification result based on the cell information IC as training data, the table Tc includes at least genome-related information IG. In this case, the table generation portion 33*c* classifies the genome-related information IG included in the table Tc on the basis of the classification model MC. The table generation portion 33*c* generates a table Tc in association with the class of the cell C on the basis of the classification result.

This cell is associated with the imaging information IB using the table Tc and this cell can be determined on the basis of the imaging information IB without directly using the cell information IC or the genome-related information IG such that the type of cell, which responds to a certain chemical, is determined.

Figure 34:
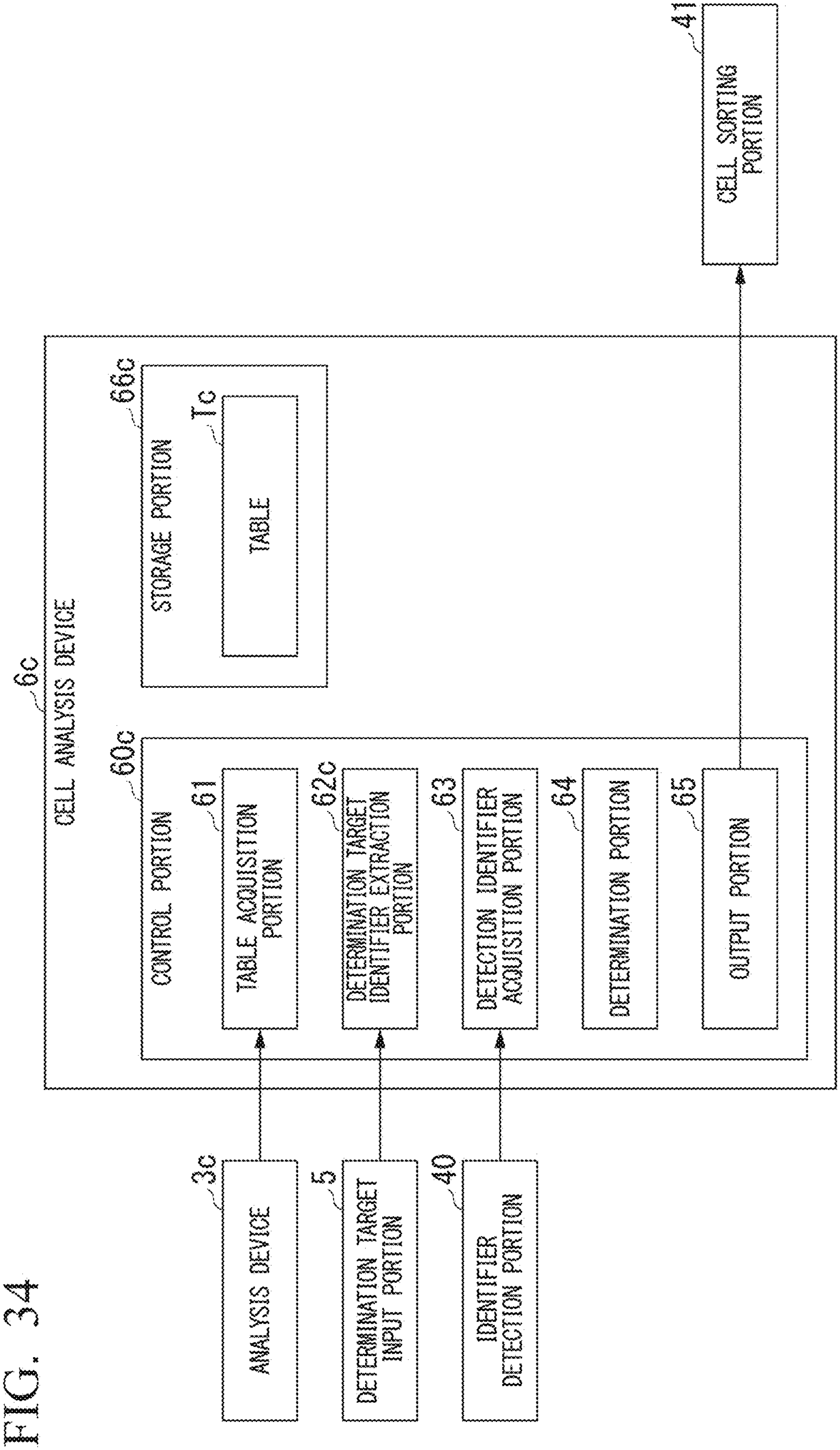
FIG. 34 is a diagram showing an example of a configuration of a cell analysis device according to the second embodiment of the present invention.

Next, a configuration of the cell analysis device 6*c* will be described with reference to FIG. 34. FIG. 34 is a diagram showing an example of the configuration of the cell analysis device 6*c* according to the present embodiment. The cell analysis device 6*c* includes a control portion 60*c* and a storage portion 66*c*.

The control portion 60*c* includes a table acquisition portion 61*c*, a determination target identifier extraction portion 62*c*, a detection identifier acquisition portion 63, a determination portion 64, and an output portion 65. When the control portion 60*c* (FIG. 34) of the cell analysis device 6*c* according to the present embodiment is compared with the control portion 30 (FIG. 11) of the cell analysis device 6 according to the first embodiment, the determination target identifier extraction portion 62*c* is different. Here, the functions of the other components (the table acquisition portion 61, the detection identifier acquisition portion 63, the determination portion 64, and the output portion 65) are the same as those of the first embodiment. Description of the functions that are the same as those in the first embodiment will be omitted and description of the second embodiment will focus on parts different from those in the first embodiment.

The determination target identifier extraction portion 62*c* extracts the determination target identifier from the table Tc acquired by the table acquisition portion 61. Here, the determination target identifier extraction portion 62*c* extracts the determination target identifier from the table Tc on the basis of a type or feature of the determination target cell CT received by the determination target input portion 5.

A table Tc is stored in the storage portion 66*c*.

Figure 35:
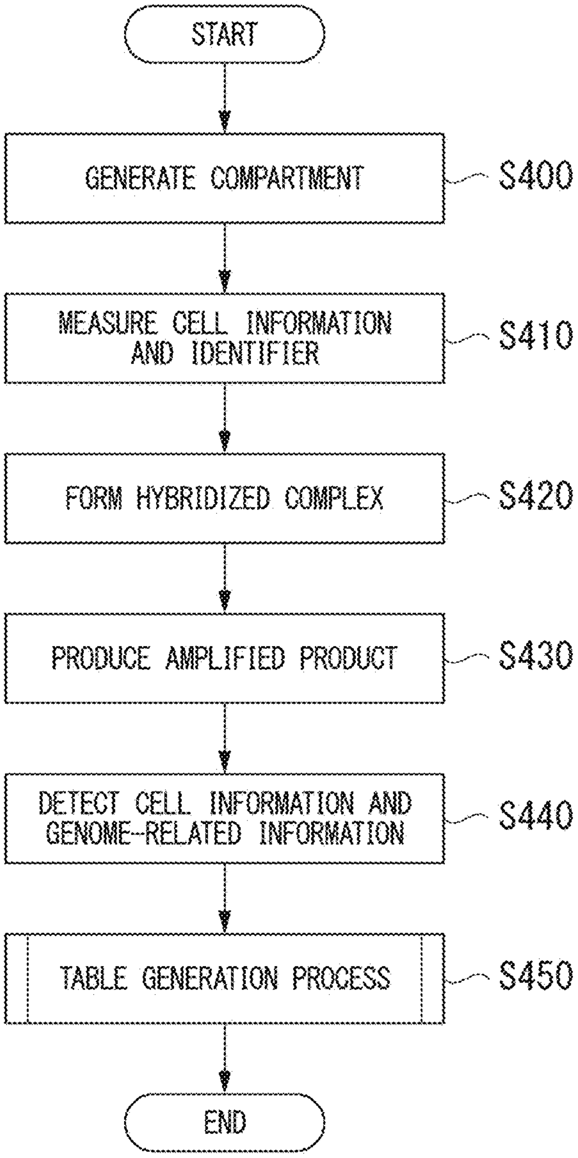
FIG. 35 is a diagram showing an example of a classification model preparation process according to the second embodiment of the present invention.

Next, a table preparation process, which is a process executed as preparation for generating the table Tc in the cell sorting system CSc, will be described with reference to FIG. 35. FIG. 35 is a diagram showing an example of the table preparation process according to the present embodiment.

Step S400: The compartment generation portion 1*c* generates a compartment Pc. Here, the compartment generation portion 1*c* generates a plurality of types of compartments Pc by combining a plurality of types of cells C, a plurality of types of first beads B1, and a plurality of types of second beads B2. The compartment generation portion 1*c* supplies the generated compartments Pc to the cell information and identifier measurement portion 2.

Step S410: The cell information and identifier measurement portion 2 measures the cell information IC of the cell C included in the compartment Pc and the imaging information IB of the first bead B1 included in the compartment Pc with respect to the compartments Pc generated by the compartment generation portion 1*c*. The cell information and identifier measurement portion 2 supplies the compartment P for which the measurement has been completed to the hybridized complex formation portion 7*c*.

Also, the cell information and identifier measurement portion 2 supplies the measured cell information IC and the imaging information IB to the analysis device 3*c*.

Step S420: The hybridized complex formation portion 7*c* forms a hybridized complex by allowing the genome-related nucleic acid of the cell C included in the compartment Pc and the first barcode nucleic acid N1 linked to the first bead B1 such that linkage is cleavable to hybridize with the second barcode nucleic acid N2 combined with the second bead B2 such that linkage is cleavable.

Here, the hybridized complex formation portion 7*c* cleaves the first barcode nucleic acid N1 from the first bead B1 having the imaging information IB associated with the cell information IC, and then allows the cell C to be dissolved. Subsequently, the hybridized complex formation portion 7*c* forms a hybridized complex by allowing each of the genome-related nucleic acid NG derived from the cell C and the first barcode nucleic acid N1 to hybridize with the second barcode nucleic acid N2 combined with the second bead B2 within the compartment Pc. Subsequently, the hybridized complex formation portion 7*c* destroys the compartment Pc.

The hybridized complex formation portion 7*c* supplies the formed hybridized complex to the amplified product production portion 8*c*.

Step S430: The amplified product production portion 8*c* produces an amplified product derived from the hybridized complex formed by the hybridized complex formation portion 7*c*. The amplified product production portion 8*c* supplies the produced amplified product to the cell information and genome-related information detection portion 9*c*.

Here, for example, when the genome-related nucleic acid NG is RNA, the amplified product production portion 8*c* causes a reverse transcription reaction to occur for the hybridized complex formed by the hybridized complex formation portion 7*c*. According to this reverse transcription reaction, for example, cDNA for mRNA derived from the cell C is synthesized and cDNA corresponding to the first barcode nucleic acid N1 is synthesized. Subsequently, the amplified product production portion 8*c* may perform template switching.

After cDNA is synthesized, the amplified product production portion 8*c* initiates a PCR reaction. Two types of amplified products, which are a first amplified product and a second amplified product, are produced in accordance with this PCR reaction. Here, the first amplified product is an amplified product derived from a hybridized complex of the first barcode nucleic acid N1 and the second barcode nucleic acid N2. The second amplified product is an amplified product derived from a hybridized complex of mRNA derived from the cell C and the second barcode nucleic acid N2.

Also, when the genome-related nucleic acid NG is DNA, extension PCR may be used as the PRC reaction.

The amplified product production portion 8*c* prepares a library of amplified products including a first amplified product and a second amplified product derived from a plurality of types of compartments Pc on the basis of the manufactured amplified products.

Step S440: The cell information and genome-related information detection portion 9*c* detects the cell information IC and the genome-related information IG in association on the basis of the amplified product produced by the amplified product production portion 8*c*.

Here, the cell information and genome-related information detection portion 9*c* integrally detects the cell information IC and the genome-related information IG using the expression pattern of the amplified product produced by the amplified product production portion 8*c* as an index. The expression pattern of the amplified product is, for example, sequence information of the amplified product, sequence information of the first barcode nucleic acid N1 in this sequence information, sequence information of the first common barcode region N11, sequence information of the second barcode nucleic acid N2, sequence information of the second common barcode region N21, sequence information of the second unique barcode region N22, and the like obtained in a sequencing process.

The cell information and genome-related information detection portion 9*c* decides on a sequence of the amplified product produced by the amplified product production portion 8*c* using a sequencer and analyzes the sequence information of the amplified product. In the analysis of the second amplified product, the sequence information of the second common barcode region N21 is used as an index to assign the cell C from which each amplified product is derived.

Also, because each mRNA can be identified using the sequence information of the second unique barcode region N22, information such as the sequence of mRNA for each cell C and its expression level can be obtained using the sequence information of the second unique barcode region N22 as an index. Transcriptome information for each cell C can be obtained on the basis of information obtained in the analysis of the second amplified product.

Subsequently, the cell information and genome-related information detection portion 9*c* analyzes the cell information IC. Here, as described above, the cell information IC is associated with the imaging information IB of the first bead B1 and the first barcode nucleic acid N1 corresponding to the imaging information IB is linked to the first bead B1. Therefore, the cell information and genome-related information detection portion 9*c* can assign the derived cell information IC of the cell C to each first amplified product on the basis of the sequence information of the first common barcode region N11 of the first barcode nucleic acid N1.

Subsequently, the cell information and genome-related information detection portion 9*c* combines the cell information IC and the genome-related information IG such as transcriptome information. Thereby, the cell information and genome-related information detection portion 9*c* associates the genome-related information IG of the cell C with the cell information IC one-to-one in each compartment Pc.

The cell information and genome-related information detection portion 9*c* supplies the detected cell information IC and the genome-related information IG to the analysis device 3*c*.

Step S450: The analysis device 3*c* executes a table generation process.

With this, the cell sorting system CSc ends the table preparation process.

Here, the table generation process executed by the analysis device 3*c* will be described with reference to FIG. 36.

Figure 36:
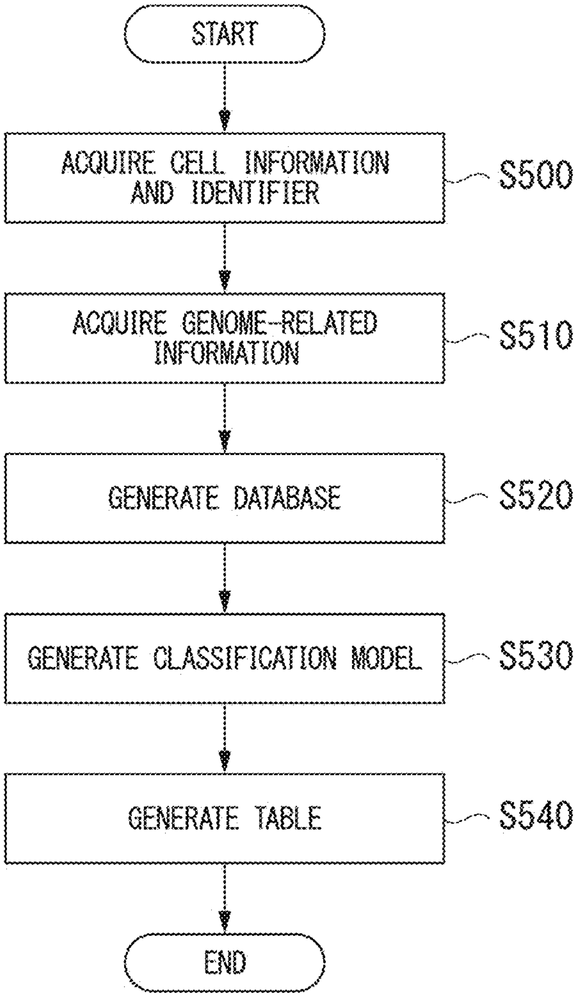
FIG. 36 is a diagram showing an example of a classification model generation process according to the second embodiment of the present invention.

FIG. 36 is a diagram showing an example of the table generation process according to the present embodiment.

Also, because the processing of step S500 is similar to the processing of step S100 in FIG. 13, description thereof will be omitted.

Step S510: The genome-related information acquisition portion 34*c* acquires the genome-related information IG associated with the cell information IC output by the cell information and genome-related information detection portion 9*c*. The genome-related information acquisition portion 34*c* supplies the acquired genome-related information IG to the database generation portion 35*c*.

Step S520: The database generation portion 35*c* generates a database DB on the basis of the cell information IC acquired by the cell information acquisition portion 31 and the genome-related information IG acquired by the genome-related information acquisition portion 34*c*. The database generation portion 35c supplies the generated database DB to the classification model generation portion 36c.

Step S530: The classification model generation portion 36c generates a classification model MC on the basis of the database DB generated by the database generation portion 35c.

Here, the classification model generation portion 36c clusters the genome-related information IG on the basis of a result of combining the cell information IC obtained by the cell information and genome-related information detection portion 9c and the genome-related information IG. The classification model generation portion 36c classifies a plurality of types of cells C into a plurality of groups in this clustering.

The classification model generation portion 36c executes supervised machine learning using sets of cell information IC and results of classifying cells C as training data. The classification model generation portion 36c learns the classes of the cells C for the cell information IC in this supervised machine learning. The classification model generation portion 36c generates the classification model MC on the basis of a learning result.

The classification model generation portion 36c supplies the generated classification model MC to the table generation portion 33c.

Also, the classification model generation portion 36c may execute supervised machine learning using the sets of the genome-related information IG and the results of classifying the cells C by classifying the cell information IC into a plurality of classes as training data. The classification model generation portion 36c learns the classes of the cells C for the genome-related information IG in this supervised machine learning. The classification model generation portion 36c may generate the classification model MC on the basis of this learning result.

Step S540: The table generation portion 33c generates a table Tc on the basis of the classification model MC generated by the classification model generation portion 36c and the table T generated by the table acquisition portion 61.

The table generation portion 33c outputs the generated table Tc to the cell analysis device 6c.

With this, the analysis device 3c ends the table generation process.

Figure 37:
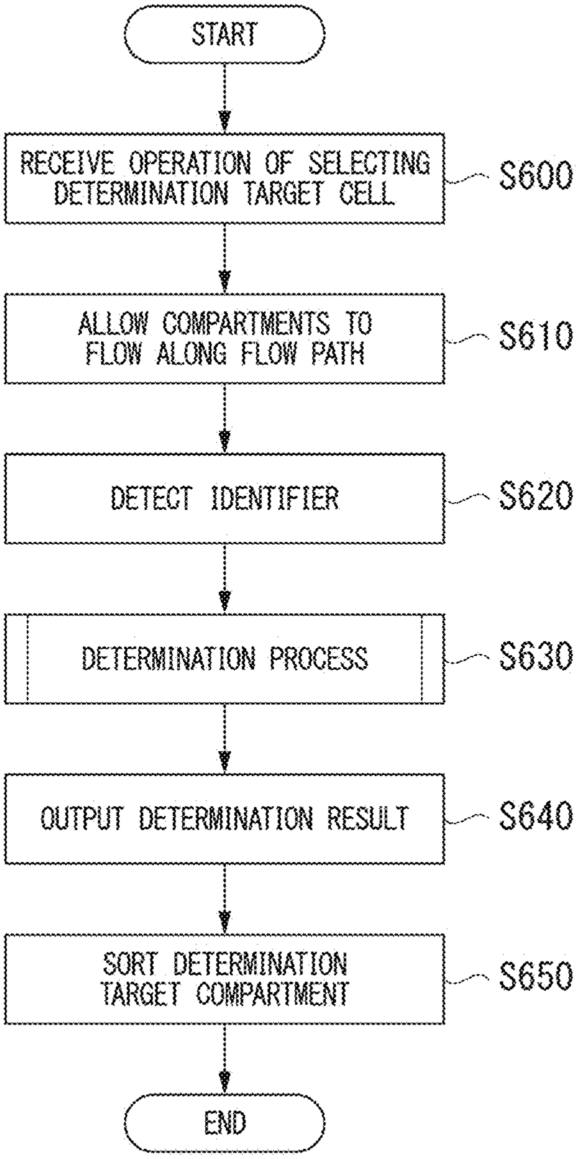
FIG. 37 is a diagram showing an example of a cell sorting process according to the second embodiment of the present invention.

Next, a cell sorting process, which is a process of sorting determination target compartments TPc in the cell sorting system CS, will be described with reference to FIG. 37. FIG. 37 is a diagram showing an example of the cell sorting process according to the present embodiment.

Also, because the processing of steps S610, S620, S640, and S650 are similar to the processing of steps S210, S220, S240, and S250 in FIG. 14, description thereof will be omitted.

Step S600: The determination target input portion 5 receives an operation in which a user of the cell sorting system CS selects a determination target cell CT. Here, in the operation of selecting the determination target cell CT, as an example, the class of the determination target cell CT is selected. The determination target input portion 5 outputs information indicating the class of the determination target cell CT to the cell analysis device 6c on the basis of the received operation.

Step S630: The cell analysis device 6c executes a determination process that is a process of determining the determination target compartment TPc. Details of the determination process will be described below with reference to FIG. 38.

Figure 38:
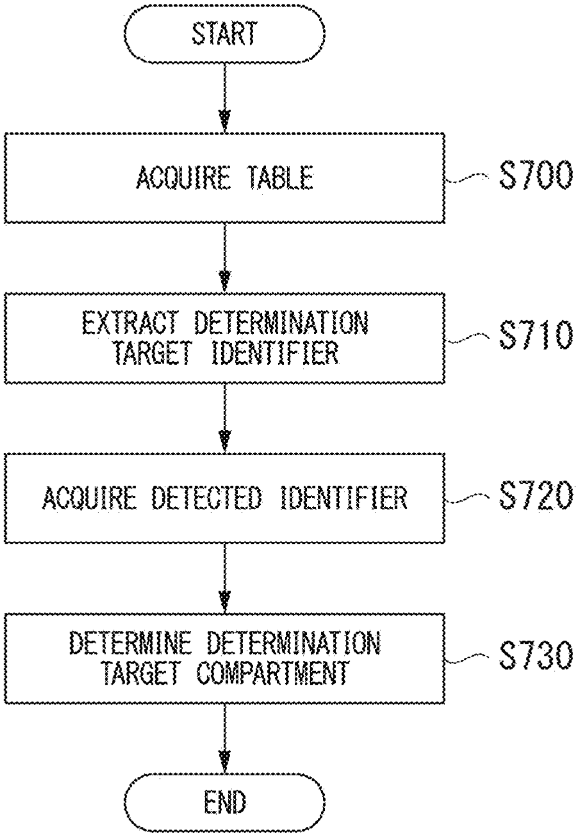
FIG. 38 is a diagram showing an example of a determination process according to the second embodiment of the present invention.

Here, the determination process of the cell analysis device 6c will be described with reference to FIG. 38. FIG. 38 is a diagram showing an example of the determination process according to the present embodiment.

Figure 15:
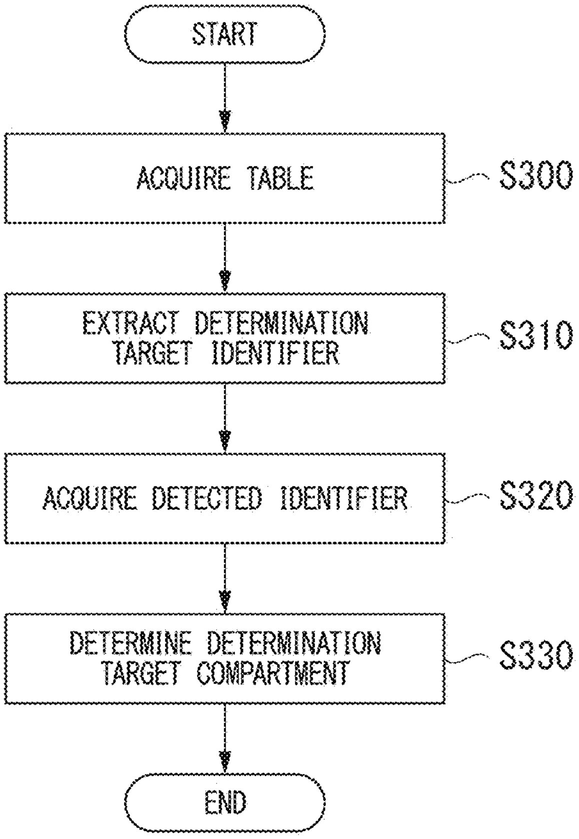
FIG. 15 is a diagram showing an example of a determination process according to the first embodiment of the present invention.

Also, because the processing of steps S700, S720, and S730 is similar to the processing of steps S300, S320, and S330 in FIG. 15, description thereof will be omitted.

Step S710: The determination target identifier extraction portion 62 extracts a determination target identifier indicating an identification substance associated with the class of the determination target cell CT received by the determination target input portion 5 from the table Tc acquired by the table acquisition portion 61. When there are a plurality of determination target identifiers indicating identification substances associated with the class of the determination target cell CT in the table Tc here, the determination target identifier extraction portion 62 extracts the plurality of determination target identifiers. In the present embodiment, the determination target identifier extraction portion 62 extracts determination target imaging information IBT from the table Tc. The determination target identifier extraction portion 62 supplies the extracted determination target imaging information IBT to the determination portion 64.

Although an example in which the first bead B1 and the second bead B2 are included together with the cell C in the compartment Pe has been described in the present embodiment, the present invention is not limited thereto. It is only necessary to include first beads B1 having imaging information IB that is information capable of being identified through imaging together with the cells C within the compartment Pc.

If the compartment Pc does not include the second bead B2, the genome-related information IG is omitted from the table Tc. Thus, the determination target cell CT is designated by the cell information IC or a group of cells classified on the basis of the cell information IC in machine learning without using the genome-related information IG such that the determination target cell CT is selected.

Also, in the cell analysis device 6c according to the present embodiment, the beads B include the first beads B1 and the second beads B2. The first bead B1 is linked to the first barcode nucleic acid N1, which is a type of nucleic acid corresponding to the imaging information IB of the first bead B1, such that linkage is cleavable. A plurality of second barcode nucleic acids N2, which are nucleic acids capable of hybridizing with the genome-related nucleic acid NG corresponding to the genome of the cell C or its expression product or the first barcode nucleic acid N1, are linked to the second beads B2.

According to this configuration, in the cell analysis device 6e according to the present embodiment, the imaging information IB of the first bead B1 is associated with the genome-related information IG of the cell C, such that the determination target cell CT can be determined on the basis of the imaging information IB associated with the genome-related information IG.

Also, when the compartment P is in a form that is not destroyed in nondestructive measurement or imaging information measurement, such as droplets or gel particles, the cell information and identifier measurement portion 2 may perform measurement again after measuring the cell information IC and the identifier D (the imaging information IB) once. The cell information and identifier measurement portion 2 can measure a time-series change in the cell information IC of the cell C by measuring the cell information IC and the identifier D (imaging information IB) at each time.

Experiment Content and Results

Experimental content and results related to the cell analysis device in the above-described embodiment will be described with reference to FIGS. 39 to 43.

The purpose of the present experiment is to identify each of the above-described alginic acid compartments (hereinafter also referred to as alginic acid units) containing the above-described fluorescent beads (especially, to identify them with high reproducibility) on the basis of the above-described fluorescence spectrum.

The content of the present experiment is as follows.

(1) Generation of alginic acid units randomly containing fluorescent beads.

(2) Measurement of the fluorescence spectrum for each alginic acid unit and identification verification of fluorescence spectra obtained by measuring a small number of alginic acid units at timings different from each other.

The conclusions of this experiment are as follows.

(1) Alginic acid units randomly containing fluorescent beads could be generated.

(2) Each alginic acid unit could be identified based on fluorescence spectra obtained by measuring at timings different from each other.

Details of the present experiment will be described below.

(1) Generation of Alginic Acid Units Randomly Containing Fluorescent Beads

Procedure 1) The following PS fluorescent beads were mixed with the alginic acid solution.

A: UV (a diameter of 2 μm, Spherotech, SPEHERO™ (FH-2042-2), 1% w/v)

B: Light Yellow (a diameter of 2 μm, Spherotech, SPEHERO™ (FP-2045-2), 1% w/v)

C: Yellow (a diameter of 1 μm, Spherotech, SPEHERO™ (FP-1552-2), 1% w/v)

Procedure 2) An alginic acid solution in which PS fluorescent beads generated in the above-described 1) were dissolved was allowed to flow through the microfluidic device (flow focusing) in the aqueous phase and alginic acid droplets containing fluorescent beads were generated by sending droplet generator oil for EvaGreen (BioRad #1864005) as the oil.

Also, this microfluidic device (flow focusing) corresponds to the compartment generation portion 1 of the above-described embodiment.

Procedure 3) The alginic acid droplets generated in the above-described 2) were changed into a gel, dropped onto a slide glass, and observed using an EVOS (registered trademark) microscope.

Figure 39:
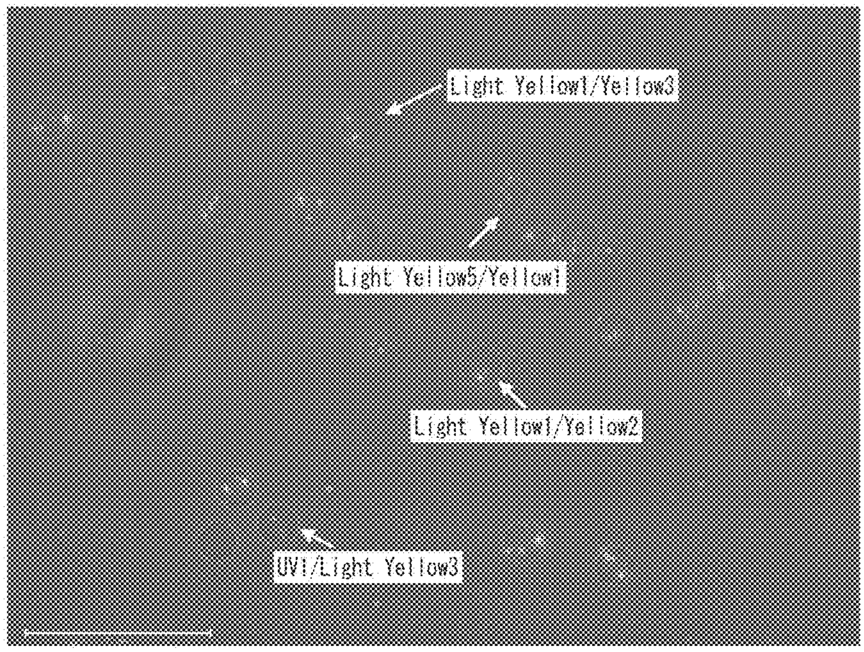
FIG. 39 is a diagram showing results of observing each alginic acid unit with a fluorescence (DAPI observation filter set/GFP observation filter set)/phase-contrast microscope.

FIG. 39 is a diagram showing results of observing each alginic acid unit with a fluorescence (DAPI observation filter set/GFP observation filter set)/phase-contrast microscope.

The generation of an alginic acid gel unit with a diameter of about 50 μm in which fluorescent beads were confined in random combinations was confirmed.

(2) Measurement of the fluorescence spectrum for each alginic acid unit and identification verification of the fluorescence spectrum obtained by measuring a small number of alginic acid units at timings different from each other.

Figure 40:
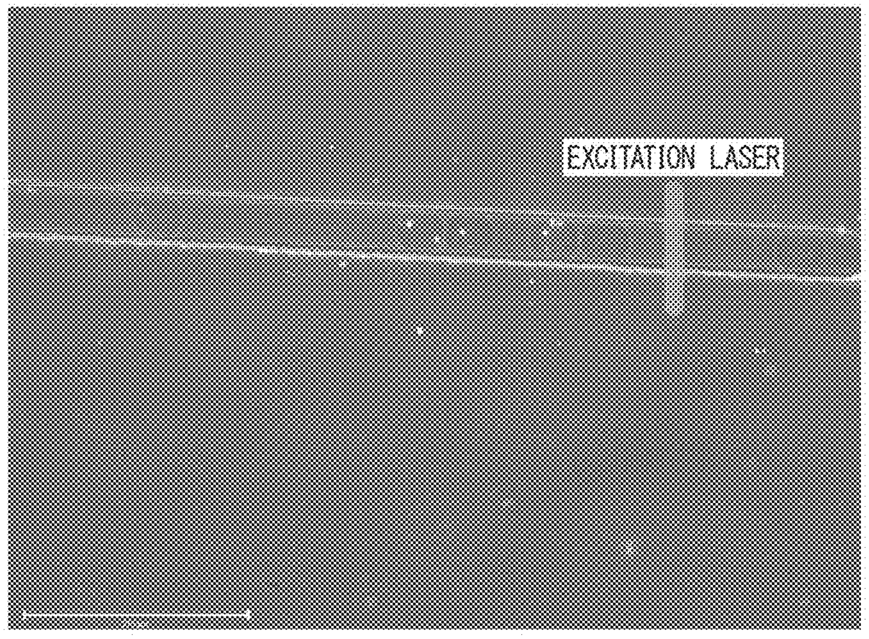
FIG. 40 is a diagram showing an example of the alginic acid unit aligned on a flow path.

FIG. 40 is a diagram showing an example of alginic acid units aligned on a flow path.

Procedure 1) The alginic acid units were aligned on the flow path. In FIG. 40, the state of alignment of alginic acid units is shown.

Procedure 2) Using a 6-ch spectrum analyzer and a moving stage, each alginic acid unit was scanned in one direction of flow path directions and a scattering signal of backscattering and a fluorescence spectrum were measured.

In the scattering signal measurement, scattered light was measured in time series by a 1-ch photomultiplier tube (PMT) using a 375 nm CW laser (Vortran, STRADUS (registered trademark) 375-60). Scattering signal measurement is measurement for detecting alginic acid units.

In the fluorescence spectrum measurement, a spectral signal was measured in time series by a 16-ch linear PMT using a 375 nm CW laser (Vortran, STRADUS (registered trademark) 375-60). Fluorescence spectroscopy is for detecting the fluorescence of the unit.

Procedure 3) Next, a measurement target sample in Procedure 2 was scanned in a direction opposite to that of Procedure 2 in a flow path direction and the scattering signal of backscattering and the fluorescence spectrum were measured in time series as in Procedure 2. An excitation wavelength for measurement is 375 nm.

Procedure 4) A time integral value of the fluorescence intensity for each channel was calculated to obtain the final fluorescence spectrum (the fluorescence intensity of each channel) for each alginic acid unit.

Figure 41:
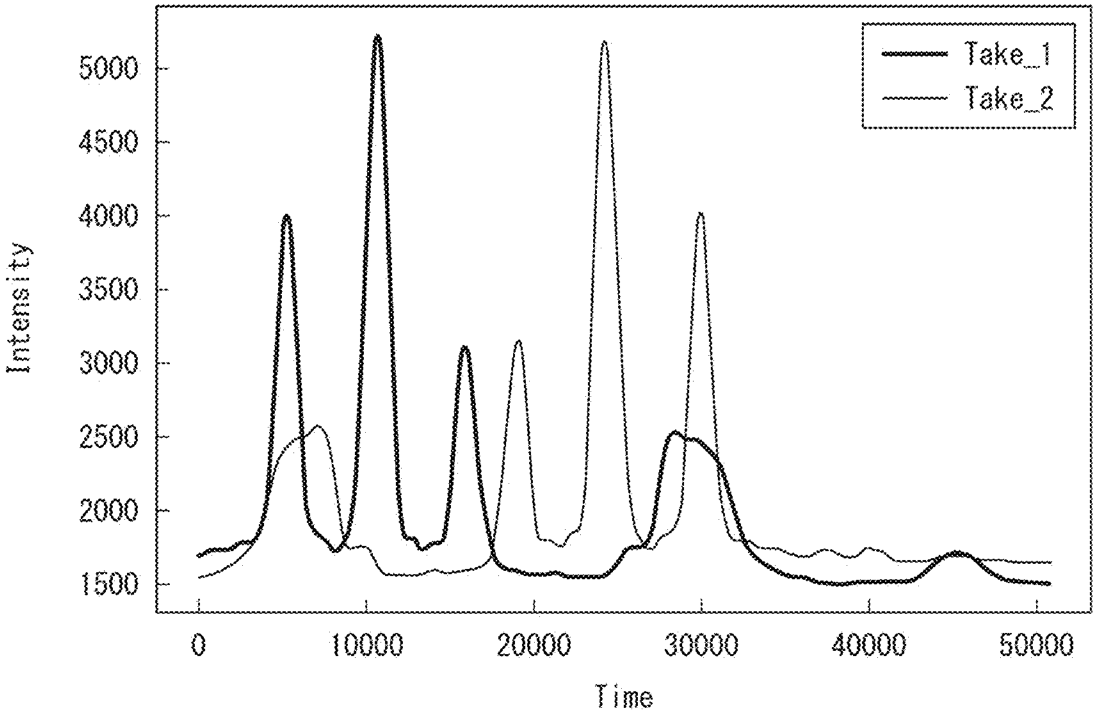
FIG. 41 is a diagram showing an example of a backscattered scattering signal detection result.

Results are shown in FIG. 41.

FIG. 41 is a diagram showing an example of a backscattered scattering signal detection result. In FIG. 41, Take_1 indicates a backscattered scattering signal detection result based on a scan of Procedure 2 (i.e., a forward scan) and Take_2 indicates a backscattered scattering signal detection result based on a scan of Procedure 3 (i.e., a reverse scan). That is, FIG. 41 shows a scattering waveform of backscattering when the alginic acid unit is measured by performing reciprocation in the flow path in the forward direction and the reverse direction. It can be seen that the alginic acid unit can be accurately detected from the fact that the scattering waveform is axisymmetric.

Figure 42:
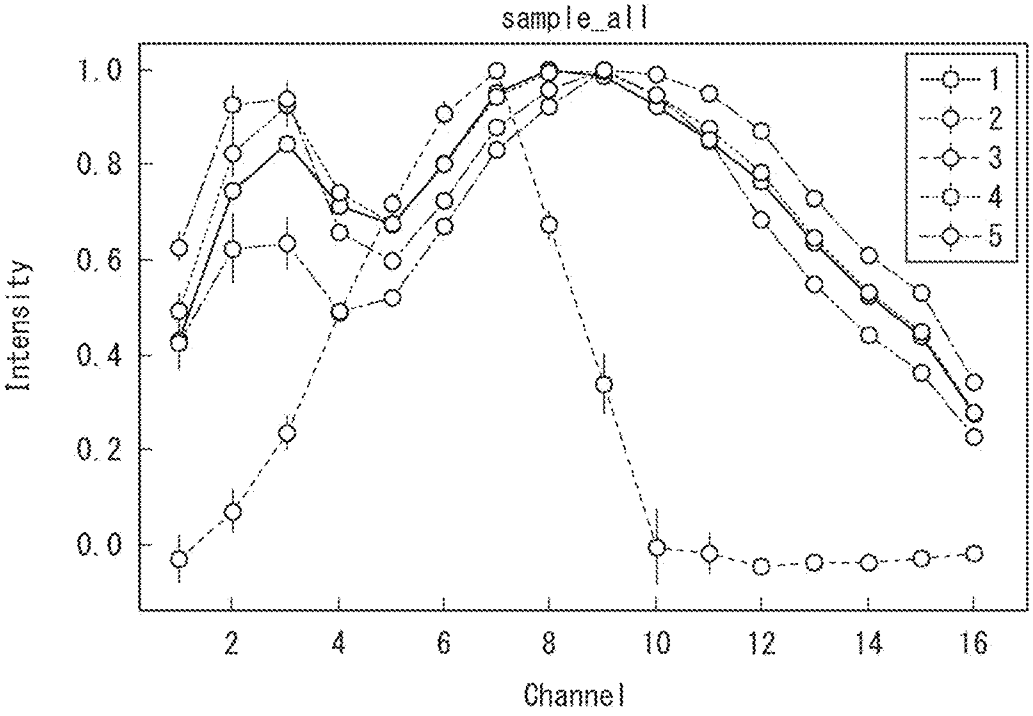
FIG. 42 is a diagram showing an example of results of calculating an average fluorescence spectrum of the same alginic acid unit measured back and forth.

FIG. 42 is a diagram showing an example of results of calculating an average fluorescence spectrum of the same alginic acid unit measured back and forth.

As shown in FIG. 42, it is shown that the same fluorescence spectrum can be obtained even if measurement is iterated because the variation (error bar) of the fluorescence spectrum of each alginic acid unit from the average value is small. Also, it is shown that the fluorescence spectra are different for each alginic acid unit.

Figure 43:
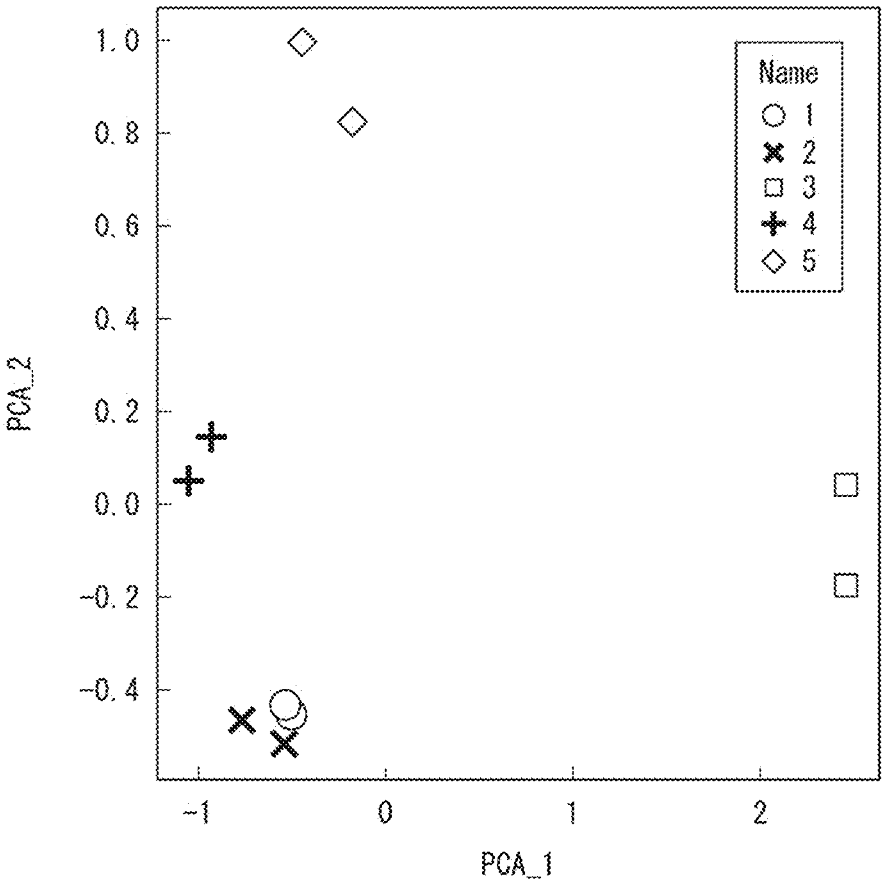
FIG. 43 shows an example of results of principal component analysis of fluorescence spectrum data.

FIG. 43 shows an example of results of principal component analysis of fluorescence spectrum data.

FIG. 43 shows results of principal component analysis (PCA) performed on fluorescence spectrum data of 10 points obtained by performing measurements associated with 5 samples twice. Because samples are arranged at positions close to each other on a coordinate plane of principal component analysis, it is shown that each alginic acid unit can be identified on the basis of the fluorescence spectrum even if measurement is performed at timings different from each other.

As described above, it is possible to identify alginic acid units accurately even after a plurality of measurements for the fluorescent beads included in the alginic acid droplets. That is, the identifier of the fluorescent bead (an example of the identification substance) can be obtained a plurality of times by the identifier acquisition portion.

In other words, when the identifier is acquired a plurality of times by the identifier acquisition portion, the compartment determination result of the determination portion does not change every time the identifier is acquired.

Also, even if identifiers are acquired at timings different from each other, alginic acid units can be identified with high reproducibility. That is, the identifier acquisition portion can acquire identifiers for the same compartment at timings different from each other.

Also, some parts of the cell analysis devices 6 and 6*c* in the above-described embodiments, for example, the table acquisition portions 61 and 61*c*, the determination target identifier extraction portions 62 and 62*c*, the detection identifier acquisition portion 63, and the determination portion 64 may be configured to be implemented by a computer. In this case, the control function may be implemented by recording a program for implementing a control function on a computer-readable recording medium and causing a computer system to read and execute the program recorded on the recording medium. Also, it is assumed that the "computer system" mentioned here is a computer system embedded in the cell analysis device 6 and includes an operating system (OS) and hardware such as peripheral devices. Also, the "computer-readable recording medium" refers to a storage device such as a flexible disc, a magneto-optical disc, a ROM, a portable medium such as a compact disc-ROM (CD-ROM), and a hard disk embedded in the computer system. Further, the "computer-readable recording medium" is assumed to include a computer-readable recording medium for dynamically retaining the program for a short period of time as in a communication line when the program is transmitted via a network such as the Internet or a communication circuit such as a telephone circuit and a computer-readable recording medium for retaining the program for a given period of time as in a volatile memory inside the computer system including a server and a client when the program is transmitted. Also, the above-described program may be a program for implementing some of the above-described functions. Further, the above-described program may be a program capable of implementing the above-described function in combination with a program already recorded on the computer system.

Also, a part or all of the cell analysis device 6 according to the above-described embodiment may be implemented as an integrated circuit of large-scale integration (LSI) or the like. Each functional block of the cell analysis device 6 may be individually implemented as a processor and some or all functional blocks may be integrated and implemented as a processor. Also, a method of implementing an integrated circuit may be implemented by a dedicated circuit or a general-purpose processor as well as LSI. Also, when integrated circuit technology with which LSI technology is replaced appears with the development of semiconductor technology, it will also be possible to use an integrated circuit based on this technology.

Although embodiments of the present invention have been described above in detail with reference to the drawings, specific configurations are not limited to the embodiments and other designs and the like may also be included without departing from the spirit and scope of the present invention.

REFERENCE SIGNS LIST

6, 6*c* Cell analysis device
62, 62*c* Determination target identifier extraction portion
63 Detection identifier acquisition portion
64 Determination portion
T, Tc Table
P, Pa, Pb, Pc Compartment
TP Determination target Compartment
MI, MIa, MIb, MIc Identification substance
C Cell
CT Determination target cell
IB Imaging information
IBT Determination target imaging information

The invention claimed is:

1. A cell analysis device comprising:
a memory; and
a processing computer that is connected to the memory and that is configured to:
extract, from a table, a determination target identifier that is information indicating an identification substance associated with a determination target cell that is a cell of a determination target, wherein the table indicates a corresponding relationship between the cell and the identification substance for each compartment with respect to compartments flowing along a flow path including the cell, the identification substance that is a substance associated with the cell, and the cell and the identification substance are spatially separated in the compartment;
acquire an identifier that is the information for identifying the identification substance included in the compartments flowing along the flow path;
determine a compartment including the determination target cell among the compartments flowing along the flow path on the basis of the acquired identifier and the extracted determination target identifier; and
output a determination result of the compartment.

2. The cell analysis device according to claim 1, wherein the identifier is information for optically identifying the identification substance, and
wherein the optically identifying the identification substance includes one or more of identifying the identification substance through imaging and identifying the identification substance by analyzing a spectrum of light emitted from the identification substance.

3. The cell analysis device according to claim 2, wherein:
the identification substance is beads having imaging information that is information capable of being identified through imaging as the identifier,
the compartment is a gel,
the identifier is a position of the identification substance within the compartment,
the identification substance is arranged at a position associated with the cell within the compartment
the compartment is divided into an upper part and a lower part in a direction perpendicular to a flow velocity direction of the flow path,
the cell is arranged in the upper part and the beads is arranged in the lower part, and
a width of the compartment in the direction is preferably approximately the same as a width of the flow path in the direction.

4. The cell analysis device according to claim 3, wherein the imaging information is optical information about one or more of a visible light absorption spectrum, dispersion, a fluorescence intensity, scattering, and a Raman spectrum.

5. The cell analysis device according to claim 3, wherein the beads include a first bead to which a first barcode nucleic acid, which is a type of nucleic acid corresponding to the imaging information, is linked such that linkage is cleavable; and a second bead to which a plurality of genome-related nucleic acids corresponding to a cellular genome or its expression product or a plurality of second barcode nucleic acids, which are nucleic acids capable of hybridizing with the first barcode nucleic acid, are linked.

6. The cell analysis device according to claim 2, wherein the identification substance includes a fluorescent molecule, and wherein the identifier is a spectrum of the identification substance, a type of the fluorescent molecule, a concentration of fluorescent molecules, or a combination of types of fluorescent molecules.

7. The cell analysis device according to claim 1, wherein the table shows a corresponding relationship between cell information indicating the cell and the identification substance for each compartment, and wherein the cell information is information obtained in high-content analysis.

8. The cell analysis device according to claim 1, wherein the processing computer is configured to acquire the identifier of the identification substance a plurality of times.

9. The cell analysis device according to claim 8, wherein the determination result of the compartment does not change every time the identifier is acquired when the processing computer has acquired the identifier of the identification substance a plurality of times.

10. The cell analysis device according to claim 1, wherein the processing computer is configured to acquire the identifier at timings different from each other with respect to the same compartment.

11. A flow cytometry system comprising a flow cytometry device; and a cell analysis device; wherein the cell analysis device comprises:

a memory; and a processing computer connected to the memory and that is configured to:

extract, from a table, a determination target identifier that is information indicating an identification substance associated with a determination target cell that is a cell of a determination target, wherein the table indicates a corresponding relationship between the cell and the identification substance for each compartment with respect to compartments flowing along a flow path including the cell, the identification substance that is a substance associated with the cell, and the cell and the identification substance are spatially separated in the compartment;

acquire, from the flow cytometry device, an identifier that is the information for identifying the identification substance included in the compartments flowing along the flow path of the flow cytometry device;

determine a compartment including the determination target cell among the compartments flowing along the flow path on the basis of the acquired identifier and the extracted determination target identifier; and output a determination result of the compartment, and wherein the flow cytometry device comprises the flow path along which the compartments flow, and detects the identifier.

* * * * *